(12) United States Patent
Kriesi et al.

(10) Patent No.: US 12,195,717 B2
(45) Date of Patent: Jan. 14, 2025

(54) CELL CULTURE DEVICE

(71) Applicants: UNIVERSITÄT ZÜRICH, Zürich (CH); NTNU-NORGES TEKNISK-NATURVITENSKAPELIGE UNIVERSITET, Trondheim (NO)

(72) Inventors: Carlo Kriesi, Trondheim (NO); Vartan Kurtcuoglu, Winterthur (CH); Anastasios Marmaras, Zurich (CH); Martin Steinert, Vikhammer (NO)

(73) Assignees: UNIVERSITÄT ZÜRICH, Zürich (CH); NTNU-NORGES TEKNISK-NATURVITENSKAPELIGE UNIVERSITET, Trondheim (NO)

( * ) Notice: Subject to any disclaimer, the term of this patent is extended or adjusted under 35 U.S.C. 154(b) by 684 days.

(21) Appl. No.: 16/610,544

(22) PCT Filed: May 4, 2018

(86) PCT No.: PCT/EP2018/061604
§ 371 (c)(1),
(2) Date: Nov. 4, 2019

(87) PCT Pub. No.: WO2018/202894
PCT Pub. Date: Nov. 8, 2018

(65) Prior Publication Data
US 2021/0340485 A1 Nov. 4, 2021

(30) Foreign Application Priority Data

May 4, 2017 (EP) .................................. 17169597
Nov. 6, 2017 (EP) .................................. 17200210

(51) Int. Cl.
*C12M 1/00* (2006.01)
*C12M 1/02* (2006.01)
(Continued)

(52) U.S. Cl.
CPC ............ *C12M 41/36* (2013.01); *C12M 23/22* (2013.01); *C12M 23/44* (2013.01); *C12M 29/04* (2013.01);
(Continued)

(58) Field of Classification Search
CPC ...... C12M 41/36; C12M 23/22; C12M 23/44; C12M 29/04; C12M 29/14; C12M 29/20;
(Continued)

(56) References Cited

U.S. PATENT DOCUMENTS 5,133,937 A * 7/1992 Frackleton ................ B01L 7/00
436/52
5,985,653 A * 11/1999 Armstrong ............. C12M 23/54
435/286.2
(Continued)

FOREIGN PATENT DOCUMENTS

CN 102112594 6/2011
CN 105392877 3/2016
(Continued)

OTHER PUBLICATIONS

Journal of Laboratory Automation, 18(6), 519-529 (Year: 2013).*
Database WPI, Week 199718, Thomson Scientific, London, GB, AN 1997-196266, XP002783626.

*Primary Examiner* — Liban M Hassan
(74) *Attorney, Agent, or Firm* — JMB Davis Ben-David

(57) ABSTRACT

The present invention relates to a cell culture device (1) for use with an optical microscope (40), comprising a housing (10) that is configured to be placed onto a stage of an optical microscope (40) in front of an objective (41) of the microscope (40), the housing (10) enclosing an internal space (11) of the housing (10), a removable flow chamber (2) enclosing an internal space (20) for accommodating a cell culture (CC) comprising living biological cells, a heater (3) arranged in the internal space (11) of the housing (10) for heating said
(Continued)

fluid medium (M) to be guided through the flow chamber (2), a first flow path (P1) arranged in the internal space (11) of the housing (10) for guiding said fluid medium (M) towards the flow chamber (2) via said heater (3), and a second flow path (P2) arranged in the internal space (11) of the housing (2) for guiding said fluid medium (M) away from the flow chamber (2), and a pump (4) for pumping said fluid medium (M) through the first flow path (P1) into the internal space (20) of the flow chamber (2) and through the second flow path (P2) out of the internal space (20) of the flow chamber (2) when the flow chamber (2) is inserted into the internal space (11) of the housing (10).

19 Claims, 15 Drawing Sheets

(51) Int. Cl.
  *C12M 1/34* (2006.01)
  *C12M 1/36* (2006.01)
  *C12M 3/00* (2006.01)
(52) U.S. Cl.
  CPC ............ *C12M 29/14* (2013.01); *C12M 29/20* (2013.01); *C12M 41/18* (2013.01); *C12M 41/48* (2013.01)
(58) Field of Classification Search
  CPC ...... C12M 41/18; C12M 41/48; C12M 29/10; C12M 41/00; C12M 41/12
  See application file for complete search history.

(56) References Cited

U.S. PATENT DOCUMENTS

| | | | | |
|---|---|---|---|---|
| 7,358,078 | B2* | 4/2008 | Chen | G01N 1/312 435/293.1 |
| 2003/0109031 | A1* | 6/2003 | Chafin | C12Q 1/6834 506/3 |
| 2006/0141623 | A1* | 6/2006 | Smith | C12M 21/08 435/366 |
| 2006/0275893 | A1* | 12/2006 | Ishii | G01N 21/75 359/398 |
| 2010/0291588 | A1* | 11/2010 | McDevitt | G01N 33/491 435/287.1 |
| 2011/0081664 | A1 | 4/2011 | Forbes et al. | |
| 2011/0229927 | A1* | 9/2011 | Larsen | C12M 41/34 435/287.1 |
| 2011/0256551 | A1* | 10/2011 | Linder | B01L 3/502738 435/7.1 |
| 2015/0044664 | A1* | 2/2015 | Sullivan | B01F 35/2115 422/69 |
| 2015/0298123 | A1* | 10/2015 | Block, III | F04B 43/0054 435/284.1 |
| 2016/0333298 | A1 | 11/2016 | Hung et al. | |
| 2017/0056880 | A1 | 3/2017 | Levner | |

FOREIGN PATENT DOCUMENTS

| | | |
|---|---|---|
| EP | 2690167 | 1/2014 |
| JP | H0951792 | 2/1997 |
| JP | 2011203272 | 10/2011 |
| KR | 20140008294 | 1/2014 |

* cited by examiner

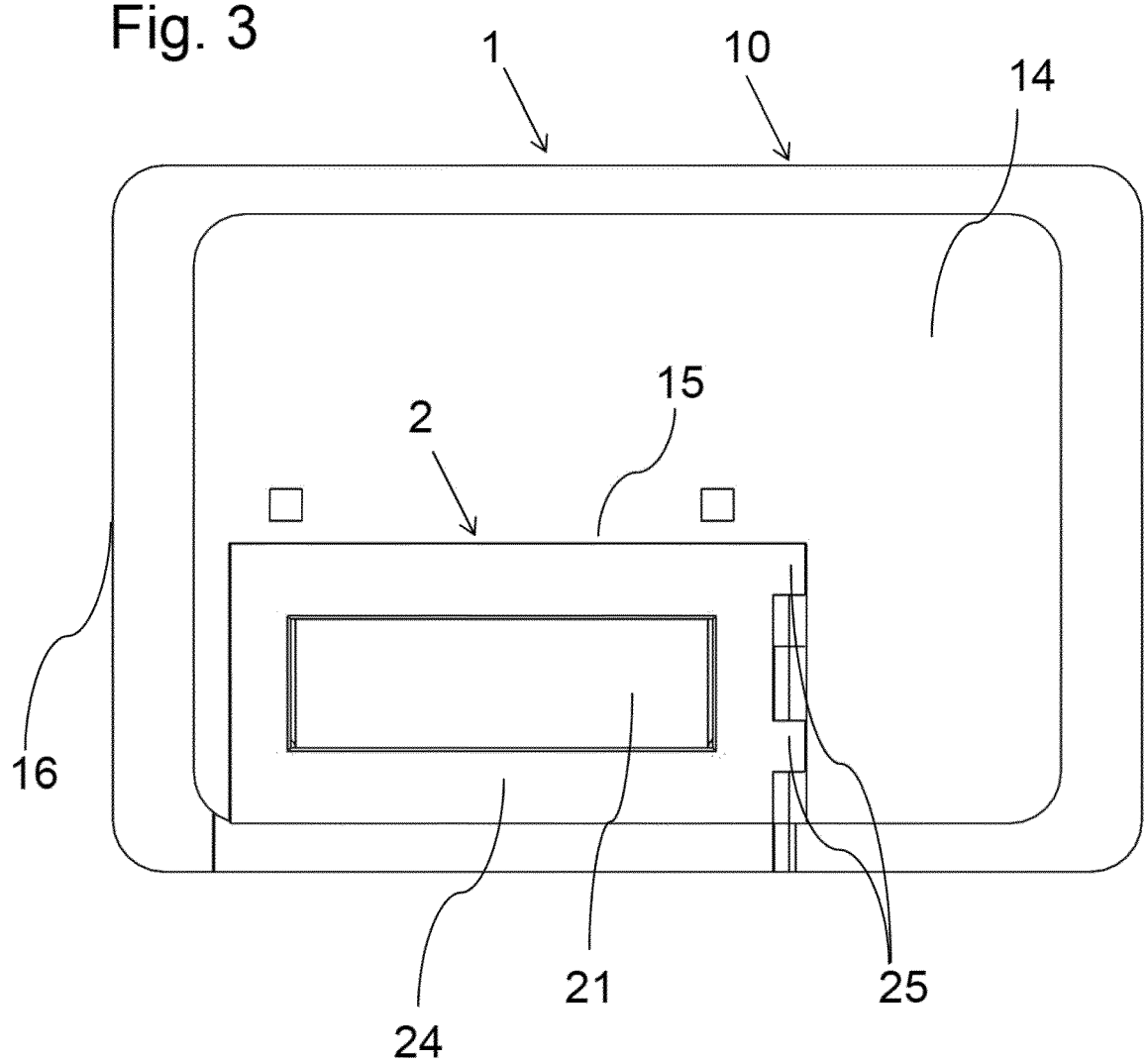

A

B

C

CELL CULTURE DEVICE

CROSS-REFERENCE TO RELATED APPLICATIONS

This is the U.S. National Stage of International Patent Application No. PCT/EP2018/061604 filed on May 4, 2018, which claims priority to European Patent Application Nos. 17169597.6 filed on May 4, 2017 and 17200210.7 filed on Nov. 6, 2017.

FIELD OF THE INVENTION

The present invention relates to a cell culture device.

BACKGROUND OF THE INVENTION

Research using living cells in vitro depends on the assumption that experimental conditions resemble those of the in vivo system under examination.

This assumption must, for obvious reasons, hold true for all experimental parameters relevant to the phenomenon under investigation.

For some of these cells, such as endothelial cells, it has been shown that their proper function depends on mechanical stimuli. To study these cells, the in vitro model needs to not only replicate the basic conditions, such as temperature and metabolism, but also replicate mechanical factors in order to produce reliable data. In order to do this, cells are placed in devices termed flow chambers, flow cells, perfusion cells or bioreactors, and exposed to flow generated by a pumping system, typically a peristaltic pump. The level of mechanical stimulus-expressed as shear stress, strain and pressure—is varied by adjusting the flow rate or dimensions of the flow chamber.

However, preparing such cell cultures for observation using an optical microscope often is a cumbersome task especially when one wants to exchange the cell culture with another one and/or needs to transport cell cultures to the microscope for observation.

BRIEF SUMMARY OF THE INVENTION

Based on the above, the problem underlying the present invention is to provide an improved cell culture device that allows to easily and efficiently observe cell cultures of the afore-mentioned kind.

This problem is solved by a cell culture device having the features of claim 1. Preferred embodiments are stated in the sub claims and are described below.

According to claim 1, a cell culture device for use with an optical microscope is disclosed, comprising

- a housing that is particularly configured to be placed onto a stage of an optical microscope below and/or above an objective of the microscope (i.e. in the light path of the microscope), the housing enclosing an internal space of the housing, wherein the housing further comprises a top wall, which top wall comprises a window, and wherein the housing comprises a bottom wall that opposes the top wall,
- a removable flow chamber enclosing an internal space for accommodating a cell culture comprising living biological cells, wherein the flow chamber is configured to be (e.g. manually or automatically) inserted into the internal space of the housing and to be (e.g. manually or automatically) removed from the housing for arranging the cell culture in the flow chamber, wherein the flow chamber is further configured for guiding a flow of a fluid medium (such as e.g. DMEM, RPMI, or artificial CSF) through the internal space of the flow chamber so that the fluid medium can contact and flow along the cell culture, and wherein the flow chamber further comprises a first and a second transparent wall region for observing the cell culture arranged in the internal space of the flow chamber between said transparent wall regions, wherein the transparent wall regions face said window when the flow chamber is inserted into said internal space of said housing,
- a heater arranged in the internal space of the housing for heating said fluid medium to be guided through the flow chamber,
- a first flow path arranged in the internal space of the housing for guiding said fluid medium towards the flow chamber via said heater, and a second flow path arranged in the internal space of the housing for guiding said fluid medium away from the flow chamber,
- a pump for pumping said fluid medium through the first flow path into the internal space of the flow chamber and through the second flow path out of the internal space of the flow chamber when the flow chamber is inserted into the internal space of the housing.

Particularly, the fact that the flow chamber can be (e.g. manually or automatically) inserted or removed from the housing means that installation or removing of the flow chamber can be accomplished without the use of tools and in a non-destructive manner. Thus, the flow chamber can be arranged in the housing and removed from the housing multiple times without significantly affecting the housing.

Thus, advantageously, the present invention provides a flow chamber system that not only provides important functionalities integrated into a single housing but can in particular also be fitted on standard microscope stages, e.g. in an embodiment it can be as small as 110 mm×160 mm×25 mm, the size of a typical microscope stage, and therefore allows for constant observation of the in vitro experiments, but also allows to easily exchange cell cultures by removing the flow chamber from the housing of the cell culture device, particularly in a tool-free manner (e.g. manually or automatically). For this, the flow chamber may be simply designed to be slid into and out of the housing of the cell culture device (see also below).

The first and the second flow path can comprise conduits, particularly flexible conduits that are arranged in the internal space of the housing. Particularly, the heater forms a section of the first flow path, wherein the heater is configured to heat said fluid medium when it passes said section.

According to an embodiment, the heater comprises a plurality of parallel heating plates. Particularly, each heating plate comprises a conductor. The respective conductor is particularly covered by a cladding of the respective heating plate, which cladding is preferably formed out of a biocompatible material, e.g. silicone. Further, the respective conductor particularly comprises a meandering shape and generates Joule heat when a voltage is applied to opposing ends of the conductor (ohmic heating). Particularly, the respective conductor is formed by a metal foil, particularly a NiCr-foil that may be cut from a blank by means of laser cutting. Particularly, said voltage is applied to the conductors in parallel. The electrical current flowing through the conductors is controlled by a control unit (see also below) which may control a transistor, particularly a MOSFET transistor, via which the electrical current coming from the conductors flows. Particularly, the transistor allows to adjust the amount of electrical current passing the transistor and thus the Joule heat generated by the conductors that heats the heating plates.

Further, particularly, the heating plates are spaced apart from one another so that a gap is provided between each two neighboring heating plates wherein the section of the first flow path that is formed by the heater starts at an inlet of heater for feeding said fluid medium into the heater, extends through the gaps and ends at an outlet of the heater from which the fluid medium is guided towards an inlet of the flow chamber (see also below).

According to an embodiment of the present invention, the cell culture device further comprises a temperature sensor arranged in the internal space of the housing so that the temperature sensor is in thermal contact with the fluid medium guided through the first flow path for measuring the temperature of the fluid medium.

In an embodiment, the cell culture device may also comprise a plurality of temperature sensors that are particularly arranged at different locations along a flow path of the fluid medium. Using several such sensors can make the control unit faster/more robust.

Particularly, the temperature sensor is arranged downstream the heater and upstream the flow chamber along the first flow path.

Further, according to an embodiment of the present invention, the cell culture device further comprises a control unit that is configured to control the heater (e.g. by controlling an electrical current flowing through the heater, e.g. via said transistor described above) such that an actual value of the temperature of the fluid medium measured with the temperature sensor approaches a desired value of the temperature of the fluid medium.

Further, according to an embodiment of the present invention, the cell culture device further comprises a flow sensor for determining a flow rate of the fluid medium. Particularly, the flow sensor can be arranged downstream the flow chamber in the second flow path.

Particularly, the control unit is configured to control said pump such that an actual value of the flow rate of the fluid medium measured with the flow sensor approaches a desired value of the flow rate of the fluid medium.

Further, according to an embodiment of the preset invention, the pump is arranged in the internal space of the housing (e.g. in the first or second flow path). Alternatively, the pump is an external pump being arranged outside said internal space of the housing.

Then, particularly, the pump may connect to a conduit via which the fluid medium is guided to an inlet of the cell culture device.

Further, according to an embodiment of the preset invention, the housing comprises a recess for inserting the flow chamber into the internal space of the housing.

Particularly, the housing comprises a lateral wall connecting the top wall to the bottom wall of the housing, wherein said recess is formed into the bottom wall and the lateral wall of the housing.

Further, according to an embodiment of the preset invention, the flow chamber is configured to be slid into the recess for inserting the flow chamber into the internal space of the housing, and configured to be slid out of the recess for removing the flow chamber from the internal space of the housing. Thus, advantageously, the flow chamber can be brought into and out of its operating position by means of simple linear sliding movement.

Further, for facilitating said sliding movement, the flow chamber comprises at least two guide rails according to a further embodiment, which guide rails are each configured to engage with an associated groove formed into the housing, so that the flow chamber can be guided by the guiding rails upon sliding the flow chamber into and out of said recess. Thus, particularly, the guide rails extend longitudinally along the sliding direction.

Further, according to an embodiment of the preset invention, the flow chamber comprises a door being hinged to an (e.g. transparent) body of the flow chamber, particularly to a first lateral side of said body, which body has a recess formed therein on a side facing the (closed) door that forms said internal space of the flow chamber and that can be closed and sealed with said door. Particularly, said door comprises said first transparent wall region, and wherein particularly said body of the flow chamber comprises or forms said second transparent wall region. Further, particularly, the door is flush with the bottom side of the housing when the flow chamber is inserted into the internal space of the housing. Particularly, the bottom side faces away from the objective of the microscope when the cell culture device is arranged with respect to said objective on a stage of the microscope. Due to the arrangement of the window on the top side of the housing and the two transparent wall regions one is able to look through the flow chamber (and the cell culture device's housing) in order to properly observe the cell culture residing in the flow chamber with said microscope.

Particularly, one of the at least two guide rails protrudes from said first lateral side of said body of the flow chamber, while the other guide rail of said at least two guide rails protrudes from a second lateral side of said body, which second lateral side faces away from the first lateral side.

Furthermore, said door comprises a latch for closing the door according to an embodiment, which latch is particularly configured to engage with a recess formed in the body for closing the door (and particularly also for sealing the internal space of the flow chamber), wherein said recess is formed into said second lateral side of the body.

Further, according to an embodiment of the preset invention, the flow chamber comprises an inlet port for injecting said fluid medium into the flow chamber and an outlet port for discharging said fluid medium out of the flow chamber. Particularly, said inlet port and said outlet port is arranged on a back side of said body of the flow chamber, which back side connects said first lateral side with said second lateral side of the body of the flow chamber.

Further, according to an embodiment of the present invention, the flow chamber further comprises a mechanism for flushing bubbles out of the flow chamber.

In an embodiment, the flow chamber comprises a first one-way valve for filling a fluid medium into the flow chamber and a second one-way valve for flushing a liquid medium as well as bubbles contained therein out of the flow chamber, wherein particularly said one-way valves are also arranged on said back side.

Further, according to an embodiment of the preset invention, the flow chamber is configured to be slid into said recess with the inlet port and the outlet port ahead so that the inlet port engages with a connector of the first flow path and the outlet port engages with a connector the second flow path and a flow connection between the inlet port and the first flow path and between the outlet port and the second flow path is established when the flow chamber is properly inserted/slid into the internal space of the housing.

Furthermore, in an embodiment of the present invention, the first flow path is connected to an inlet arranged on the housing, particularly on the top wall of the housing, while the second flow path is particularly connected to an outlet arranged on the housing, particularly on the top wall of the housing. Further, particularly, the inlet is configured to be connected to a first conduit for guiding said fluid medium into the first flow path via said inlet, while the outlet is particularly configured to be connected to a second conduit for discharging said fluid medium coming from the flow chamber out of the second flow path.

According to an embodiment, the first conduit may connect to a container for storing said fluid medium while the second conduit may connect to a waste bin for discarding the fluid medium. Alternatively, both conduits may connect to said container for recycling the fluid medium, i.e. the fluid medium is pumped into the internal space of the flow chamber via the first flow path and out of the internal space of the flow chamber back into the container via the second flow path. Particularly, the pump can be arranged in the first and or second flow path inside the internal space of the housing, or to the first conduit outside the housing of the cell culture device.

Further, according to yet another embodiment of the preset invention, the height of the housing is smaller than or equal to 25 mm. This allows one to fit the cell culture device onto a stage of a regular optical microscope. Thus, advantageously, the present invention can be used with standard microscopes and does not need dedicated optical instruments for observation of the cell cultures residing in the flow chamber.

Further, in an embodiment the breadth of the housing is smaller than or equal to 160 mm. Further, in an embodiment, the depth of the housing is smaller than or equal to 110 mm.

Furthermore, according to an embodiment of the cell culture device according to the present invention, the cell culture device comprises a bubble trap configured for removing bubbles of a gaseous phase (e.g. air or components thereof) from the fluid medium.

Particularly, according to an embodiment, the bubble trap comprises a first and a second volume, wherein the first and the second volume are separated by a semi-permeable membrane which is impermeable to the fluid medium but permeable for said gaseous phase, so that bubbles of the gaseous phase can rise from the first volume via the membrane into the second volume so as to remove them from the fluid medium. Particularly, the membrane may comprise PTFE.

Furthermore, according to an embodiment, the first volume forms a section of the first flow path, so that the gas bubbles are removed from the fluid medium in the first flow path, i.e. downstream the heater and upstream the flow chamber.

Further, according to an embodiment, the first volume of the bubble trap comprises an inlet connected to an outlet of the heater. Furthermore, according to an embodiment, the first volume comprises an outlet connected to said connector of the first flow path via which connector the flow chamber can be connected to the first flow path. Thus, the fluid medium can be passed from the heater to the first volume of the bubble trap and from the first volume to the flow chamber, wherein, when the fluid medium passes the first volume, bubbles of said gaseous phase can rise from the first volume into the second volume via the membrane so as to remove them from the fluid medium/first flow path.

Furthermore, according to an embodiment, the second volume of the bubble trap is smaller than the first volume.

Further, according to an embodiment the second volume of the bubble trap comprises a smaller pressure than the first volume. Particularly, the second (e.g. smaller) volume is under a vacuum, therefore increasing the amount of gas (e.g. air) that can pass through the semi-permeable membrane.

Further, according to an embodiment, the second volume of the bubble trap comprises an outlet for removing said gaseous phase from the bubble trap. Particularly, according to an embodiment, a pump, particularly a vacuum pump, is connected to said outlet for removing said bubbles via the pump.

Furthermore, according to yet another aspect of the present invention, a method for observing a cell culture using a cell culture device according to the present invention and a microscope is disclosed, wherein a cell culture is arranged in the flow chamber and the flow chamber is inserted into the internal space of the housing of the cell culture device, and wherein the housing of the cell culture device is arranged on a stage of the microscope below and/or in front of an objective of the microscope. Furthermore, particularly, a fluid medium is guided through the flow chamber arranged in the internal space of the housing of the cell culture device, wherein particularly the temperature is adjusted to a desired value and/or the flow rate is adjusted to a desired value.

BRIEF DESCRIPTION OF THE DRAWINGS

Further features and embodiments of the present invention are described below with reference to the Figures, wherein

FIG. 2B shows the housing with inserted control unit; FIG. 2A also indicates flow paths of a fluid medium that is guided through the flow chamber;

FIG. 3 shows a plan view onto a bottom wall of the housing of the cell culture device according to the present invention;

DETAILED DESCRIPTION OF THE INVENTION

Figure 1:
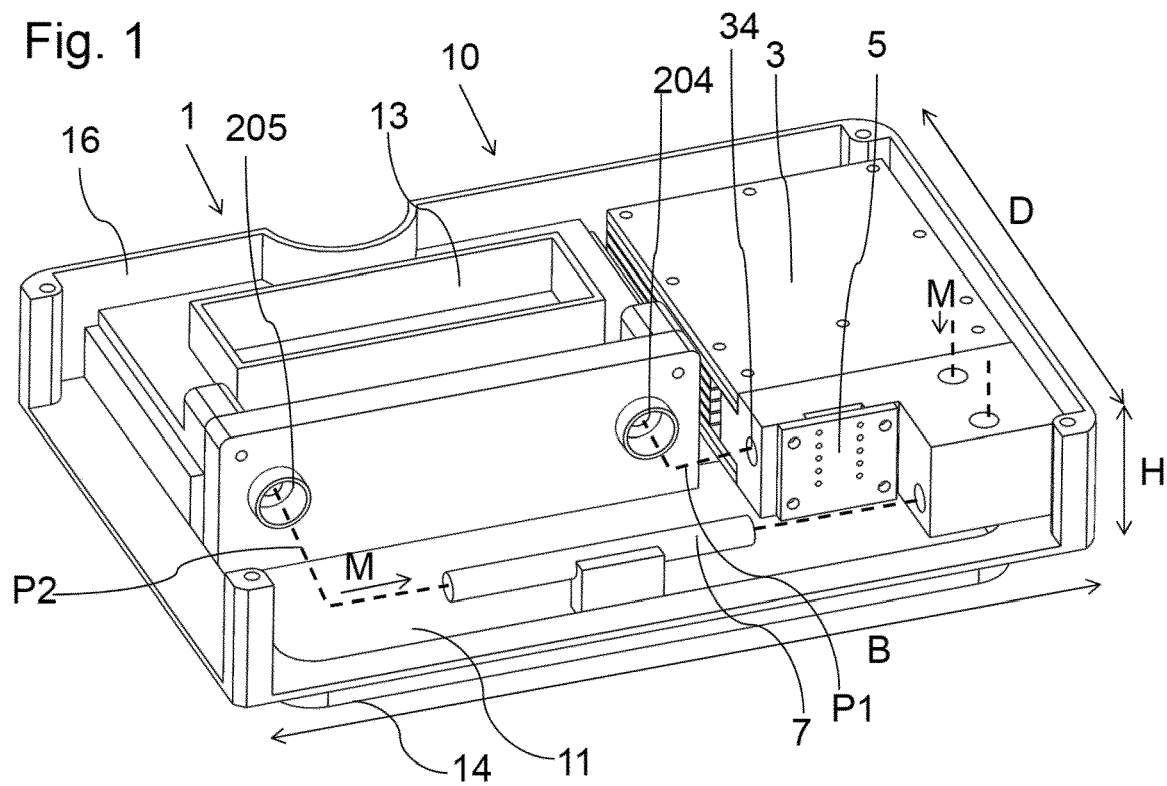
FIG. 1 shows a perspective view of a cell culture device according to the invention comprising an inserted flow chamber, wherein parts of a circumferential lateral wall and a top wall of a housing of the device are omitted to visualize an internal space of the housing of the device.
Figure 2A:
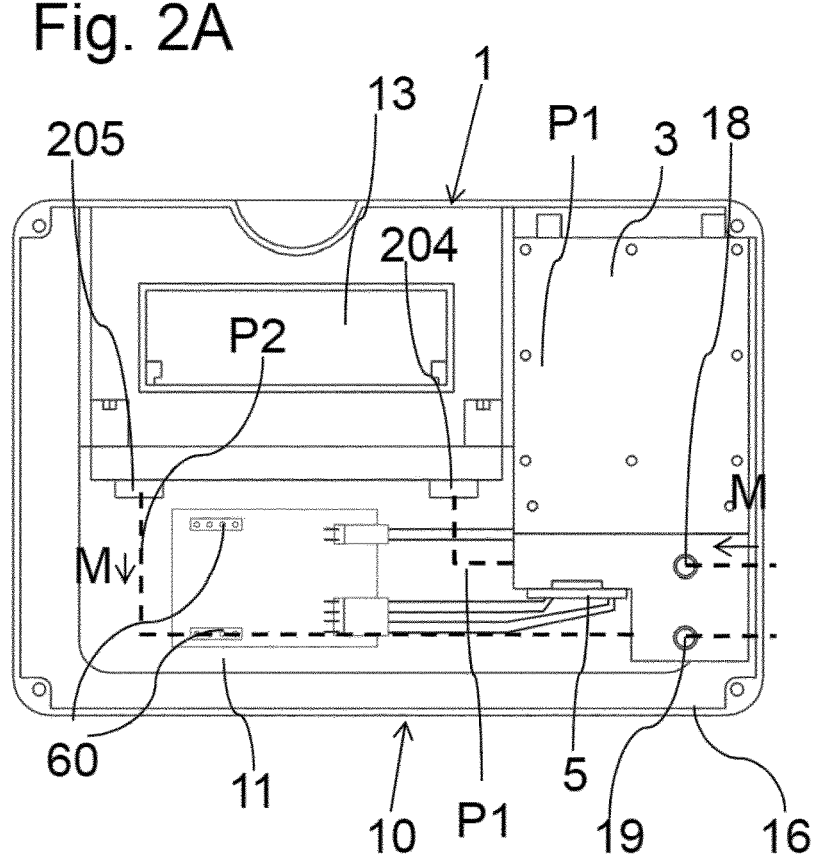
FIG. 2A-2B shows illustrations of the housing with mounted components, such as a temperature sensor and a control unit, wherein in FIG. 2A the control unit is not shown so that the connectors for making electrical contact to the control unit can be seen.
Figure 2B:
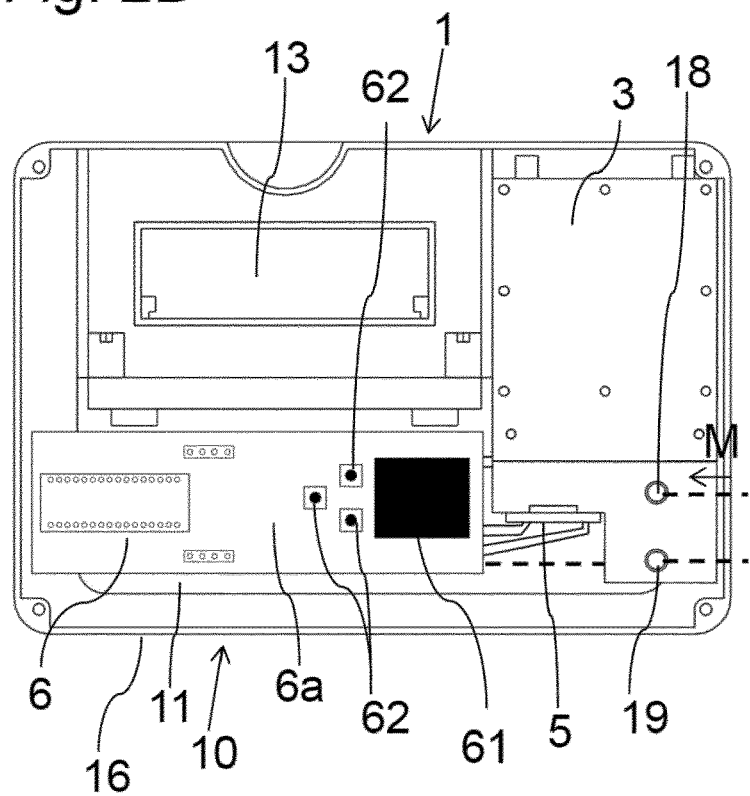
Figure 13:
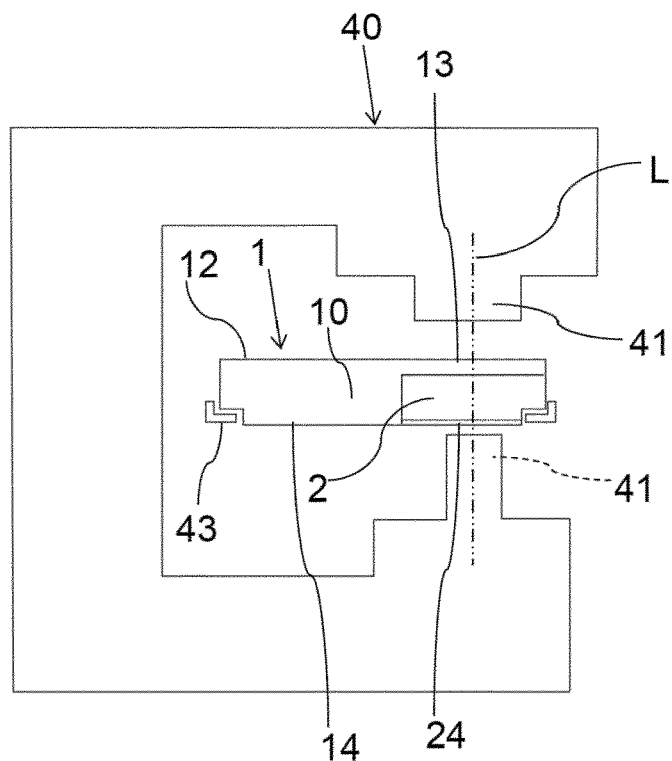
FIG. 13 shows a lateral view of the housing of the cell culture device arranged on a stage of a microscope.
Figure 14:
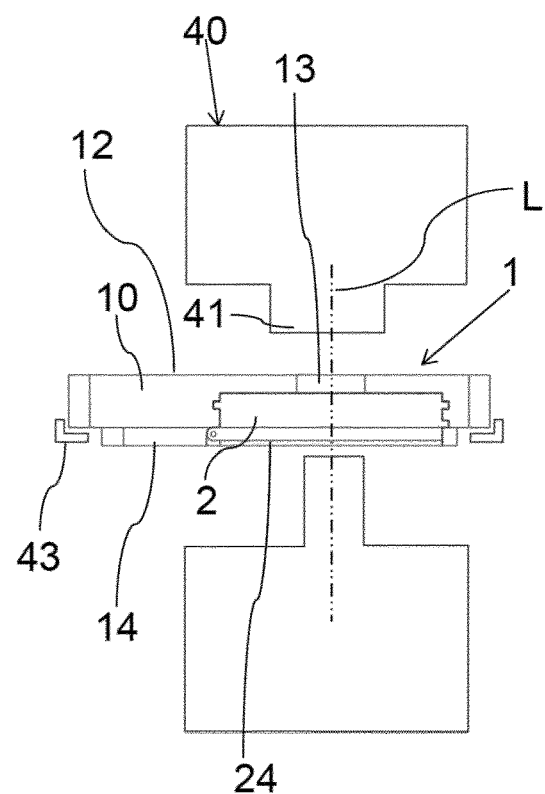
FIG. 14 shows a front view of the cell culture device and microscope shown in FIG. 13.

FIG. 1 shows in conjunction with FIGS. 2A and 2B as well as FIGS. 3 to 16 a cell culture device 1 for use with an optical microscope 40. According to FIG. 1 the cell culture device 1 comprises a housing 10 that is configured to be placed onto a stage 43 of an optical microscope 40, so that it is arranged in the light path L of the microscope 40 (i.e. in front of an objective 41 of the microscope 40) as schematically shown in FIGS. 13 and 14. The housing 10 may be arranged below the objective 41 of the microscope 40. Alternatively, the objective 41 may also be arranged below the housing 10 as indicated by the dashed line in FIG. 11.

The housing 10 encloses an internal space 11, wherein the housing 10 further comprises a top wall 12 (not shown in FIG. 1) that comprises a window 13 for observing a removable flow chamber, and an opposing bottom wall 14 (cf. FIG. 14). The removable flow chamber 2 (cf. particularly FIGS. 6 to 8) encloses an internal space 20 for accommodating a cell culture CC comprising living biological cells (e.g. endothelial cells; epithelial cells; glial cells; neurons; co-cultures, i.e. several cell types cultured at once, e.g. neuronal and glial cells; endothelial cells and fibroblast; etc.) as well as a flow of a fluid medium M (see also above), wherein the flow chamber 2 is configured to be inserted into the internal space 11 of the housing 10 and to be removed from the housing 10 for arranging the cell culture CC to be examined in the flow chamber 2. In order to maintain the cell culture CC in proper conditions, the flow chamber 2 is further configured for guiding said flow of a fluid medium M through the internal space 20 of the flow chamber 2 so that the fluid medium M can contact and flow along the cell culture CC. Particularly, one thereby aims at applying a defined force/stress on the cell culture in order to more accurately replicate in-vivo conditions of the cell culture CC. Further, the flow chamber 2 comprises a first and a second transparent wall region 21, 22 for observing the cell culture CC arranged in the internal space 20 of the flow chamber 2, wherein the transparent wall regions 21, 22 face said window 13 when the flow chamber 2 is inserted into said internal space 11 of said housing 10, so that cell culture CC can be properly observed through the window 13 and the second transparent wall region 22 while proper lighting can e.g. be applied via the first wall region 21 (e.g. FIG. 3) from below. The dimensions H×D×B as shown in FIG. 1 are preferably chosen such that the housing 10 fits onto a stage 43 of a usual microscope 40 (and at the same time below and/or in front of an objective 41 of said microscope 40). Therefore, in an example, said dimensions H×D×B can be smaller or equal to 25 mm×110 mm×116 mm.

Further, in order to adjust the temperature of the fluid medium M to a desired value, the device 1 further comprises a heater 3 arranged in said internal space 11 of the housing 10. The heater 3 forms part of a first flow path P1 (cf. FIG. 2A) arranged in the internal space 11 of the housing 10 for guiding said fluid medium M towards the flow chamber 2 (via said heater 3). The device 1 further comprises a second flow path P2 (cf. FIG. 2A) arranged in the internal space 11 of the housing 2 for guiding said fluid medium M away from the flow chamber 2. Said flow paths P1, P2 may comprise conduits, particularly flexible conduits, that are arranged in said internal space 11 of the housing 10 (e.g. along the dashed lines of FIG. 2A or FIG. 16 outside the heater 3 and flow chamber 2).

Figure 16:
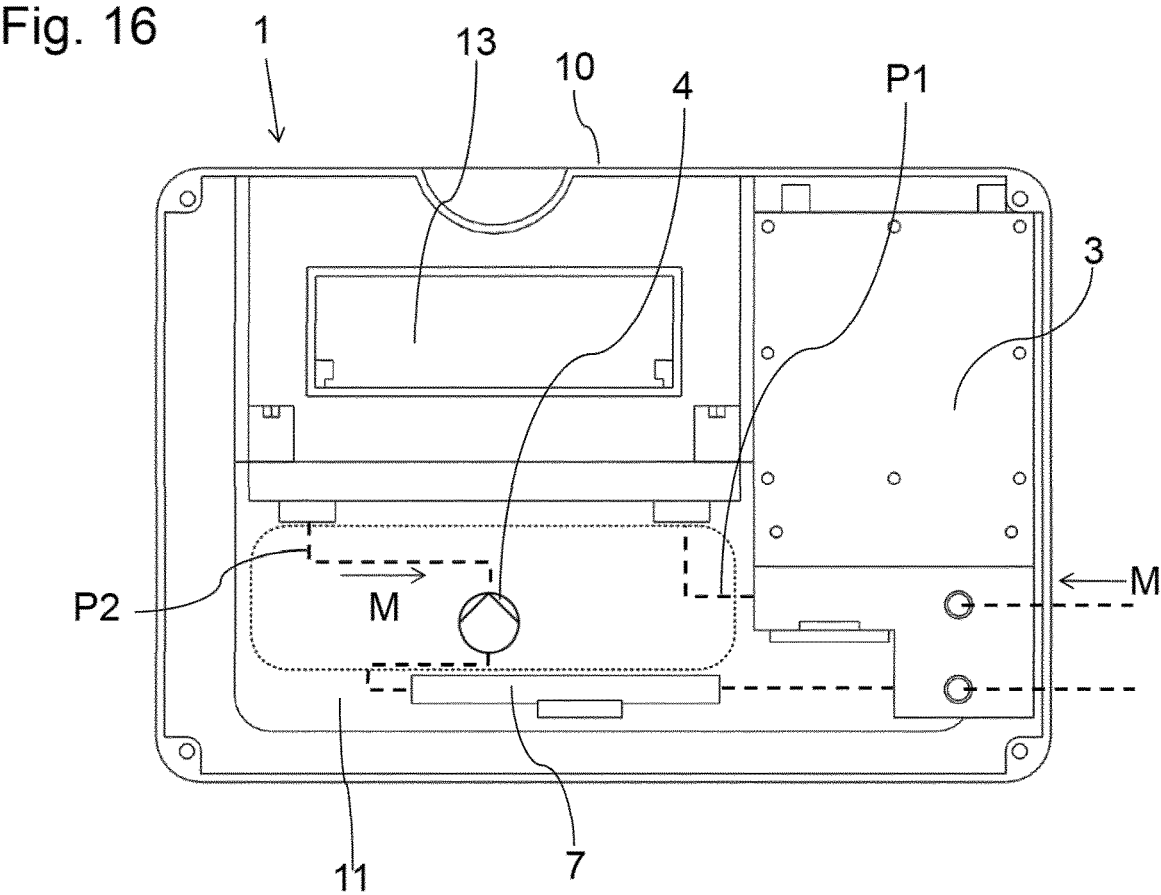
FIG. 16 shows an internal pump of the cell culture device.

Further, the device 1 comprises an (internal or external) pump 4 for pumping said fluid medium M through the first flow path P1 into the internal space 20 of the flow chamber 2 and through the second flow path P2 out of the internal space 20 of the flow chamber 2 when the flow chamber 2 is inserted into the internal space 11 of the housing 10. Particularly the fluid medium M can be pumped in a circular flow and is continuously recycled through said heater 3 and flow chamber 2. Particularly, as shown in FIG. 16, the pump 4 can be arranged in the internal space 11 of the housing 10 and may form part of the second flow path P2. Particularly the pump 4 may be arranged downstream the flow chamber 2.

In order to control (e.g. closed-loop) the temperature of the fluid medium M, the cell culture device 1 may further comprise a temperature sensor 5 arranged in the internal space 11 of the housing 10 so that the temperature sensor 5 is in thermal contact with the fluid medium M guided through the first flow path P1 for measuring the temperature of the fluid medium M. Particularly, the temperature sensor 5 is arranged downstream the heater 3 and upstream the flow chamber 2 along the first flow path P1 so that it can measure the actual temperature of the fluid medium M when the latter leaves the heater 3.

This closed-loop control is conducted by a control unit 6 that is configured to control the heater 3 such that an actual value of the temperature of the fluid medium M measured with the temperature sensor 5 approaches a desired value of the temperature of the fluid medium M. The control unit therefore receives the current temperature of the fluid medium M from the temperature sensor 5 (or from several temperature sensors) as an input.

FIG. 2A shows a top view of the cell culture device 1 with a circuit board 6a of the control unit 6 removed from the internal space 11 of the device 1 so that the connectors 60 for the printed circuit board 6a/control unit 6 can be seen. FIG. 2B shows the device 1 with the mounted circuit board 6a and control unit 6 thereon, which circuit board 6a also comprises a display 61 for e.g. displaying a selected desired temperature (or other selected desired quantities such as a desired flow rate of the fluid medium) as well as operating elements (e.g. buttons 62) to manually operate the control unit 6 (e.g. for selecting desired quantities such as a desired temperature or a desired flow rate).

Figure 9:
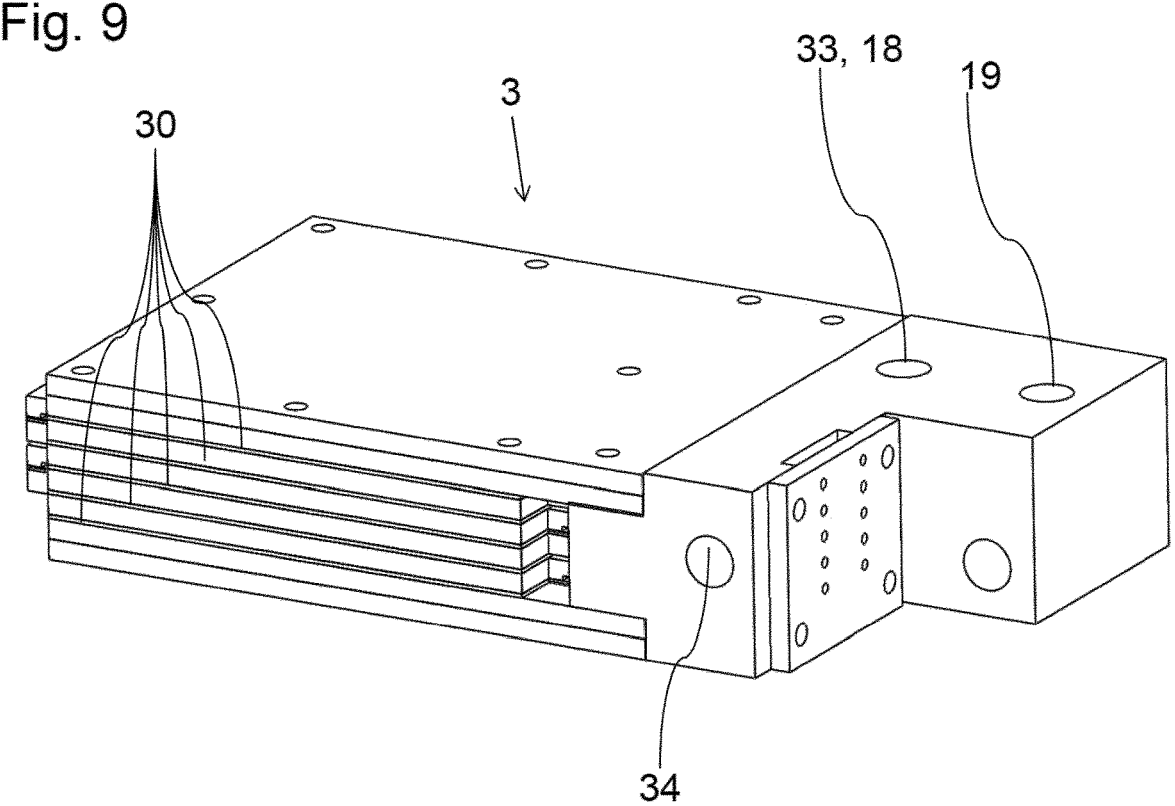
FIG. 9 shows a perspective view of a heater of the cell culture device according to the present invention.
Figure 10:
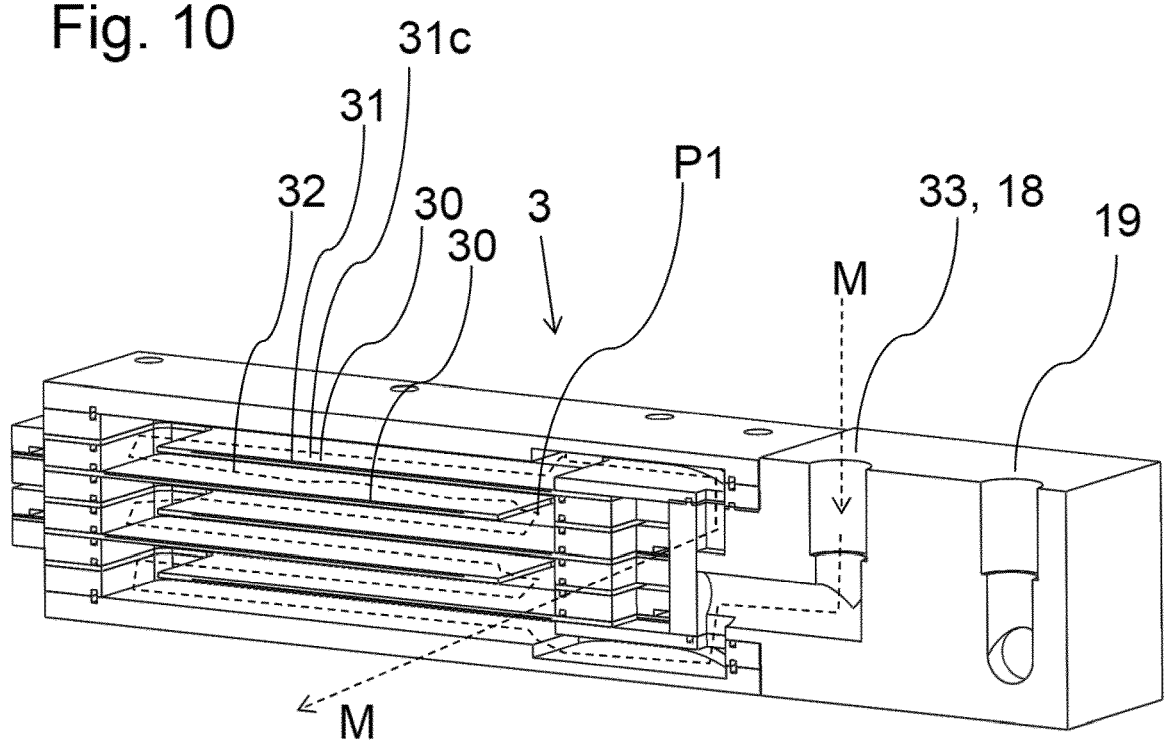
FIG. 10 shows a perspective cross sectional view of the heater.
Figure 11:
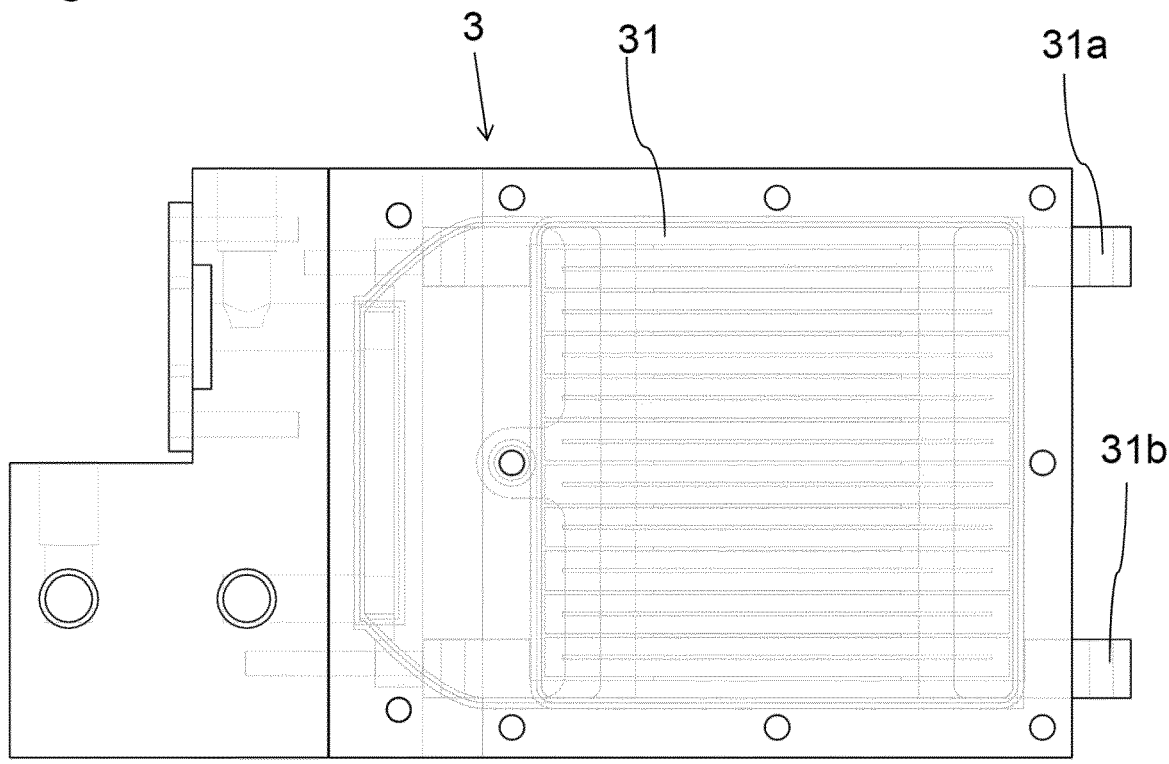
FIG. 11 shows a top view onto the heater, wherein a conductor for ohmic heating of an upper heating plate of the heater is indicated.
Figure 12:
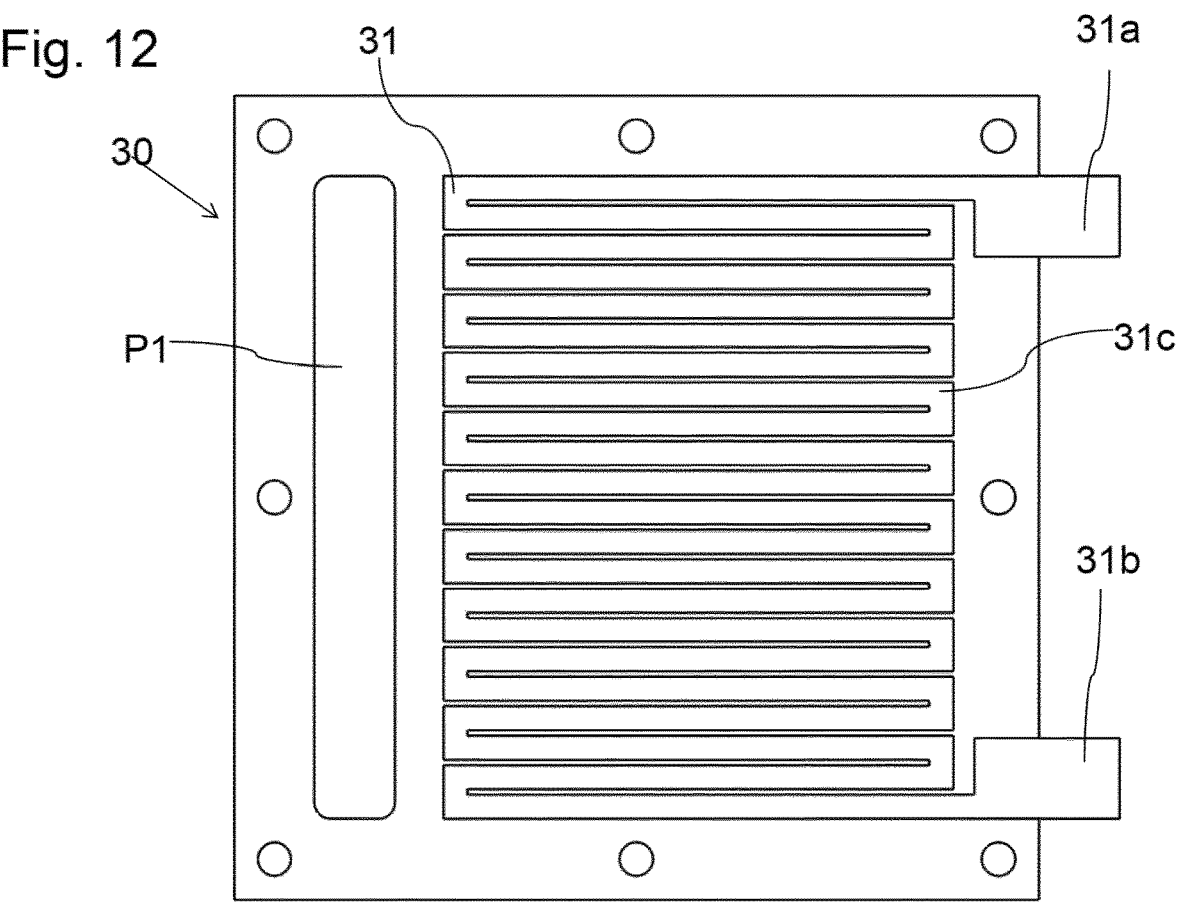
FIG. 12 shows a heating plate of the heater shown in FIG. 11.

For ohmic heating of the fluid medium M, the heater 3 may comprise a plurality of parallel heating plates 30 as shown in FIGS. 9 to 12 that comprise a cladding 31c formed out of an e.g. biocompatible material. A conductor 31 is embedded in said cladding 31c of the respective heating plate 30, wherein the respective conductor 31 particularly comprises a meandering shape as indicated in FIGS. 11 and 12 and generates Joule heat when a voltage (e.g. a direct-current voltage, e.g. 19V) is applied to opposing ends or contacts 31*a*, 31*b* of the respective conductor 31 (ohmic heating). Particularly, the respective conductor 31 is formed by a metal foil, particularly a NiCr-foil, that may be cut from a blank by means of laser cutting. Particularly, said voltage is applied to the conductors 31 in parallel. The electrical current flowing through the conductors 31 is controlled by the control unit 6 described above which may particularly control a transistor, particularly a MOSFET transistor, via which the electrical current coming from the conductors 31 flows. Particularly, the transistor allows to adjust the amount of electrical current passing the transistor and thus the Joule heat generated by the conductors 31 that heat the heating plates 30. Particularly, FIG. 12 shows one of the heating plates 30 indicating said cladding 31*c* and the conductor 31 being covered by said cladding 31*c*, Further, said contacts 31*a*, 31*b* protrude out of said cladding 31*a* so that an electrical current can be applied to the contacts 31*a*, 31*b*. As also indicated in FIG. 12, the heating plate 30 comprises a recess which forms part of the first flow path P1 (cf. also FIG. 10).

Figure 6:
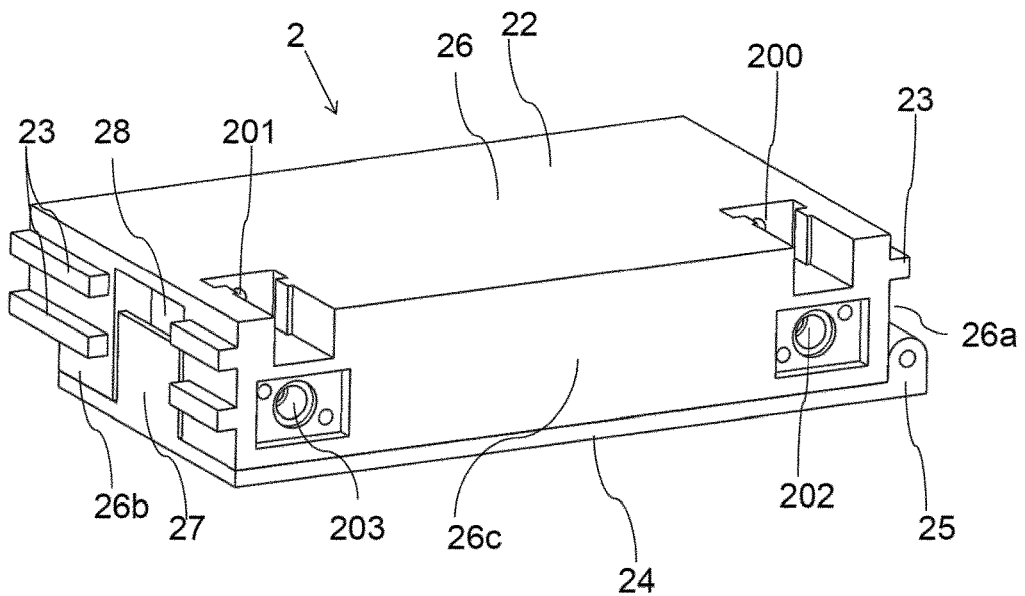
FIG. 6 shows a perspective view of the flow chamber.
Figure 8:
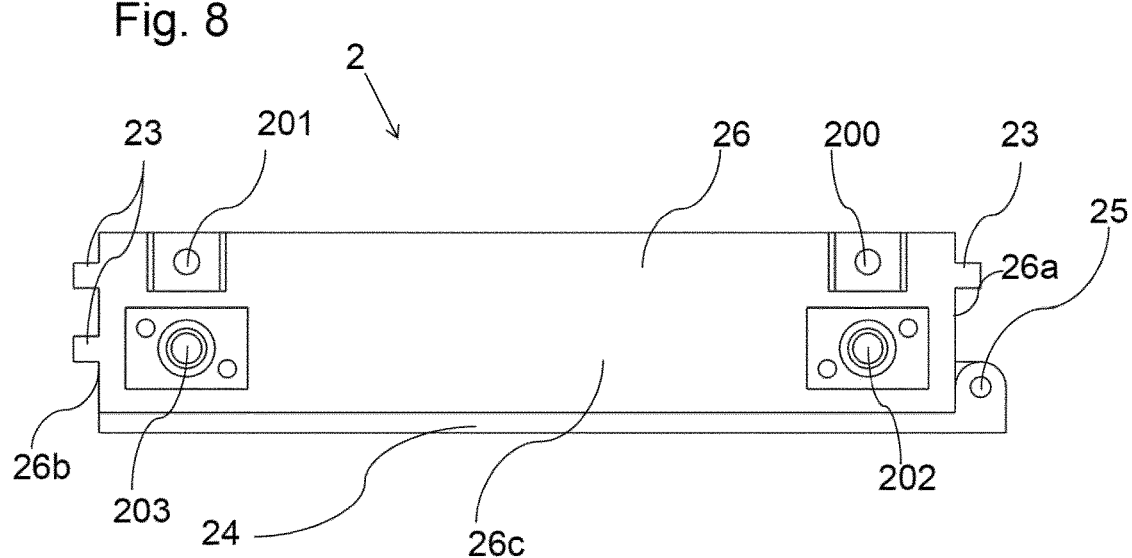
FIG. 8 shows a side view of the flow chamber (onto a back side of a body of the flow chamber)

As can be seen in FIGS. 9 and 10, the heating plates 30 are spaced apart from one another so that a gap 32 is provided between each two neighboring heating plates 30 wherein the section of the first flow path P1 that is formed by the heater 3 starts at an inlet 33 of heater 3 for feeding said fluid medium M into the heater 3, extends through the stacked gaps 32 along the dashed line in FIG. 10 and ends at an outlet 34 of the heater 3 (cf. e.g. FIG. 9) from which the fluid medium M is guided towards an inlet 200 of the flow chamber 2 which is shown in FIGS. 6 and 8 in particular.

Furthermore, the cell culture device 1 further comprises a flow sensor 7 for determining a flow rate of the fluid medium M (cf. FIG. 1). Such a flow sensor 7 can be placed upstream and/or downstream the flow chamber 2, Here, as example, the flow sensor 7 is arranged in the second flow path P2 downstream the flow chamber 2 in the internal space 11 of the housing 10. Determining the flow rate allows one to precisely tune the shear forces acting on the cell culture CC via the flowing medium M. For this, the control unit 6 is configured to control said pump 4 such that an actual value of the flow rate of the fluid medium M measured with the flow sensor 7 approaches a desired value of the flow rate of the fluid medium M.

Figure 4:
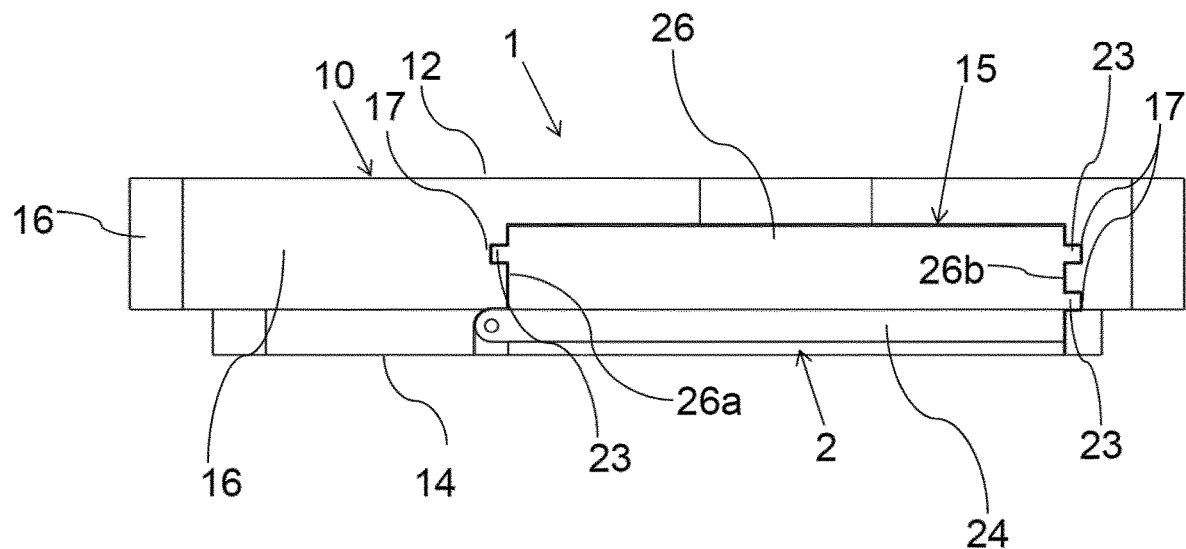
FIG. 4 shows a side view onto a lateral wall of the housing, which lateral wall comprises, together with the bottom wall, a recess for inserting the flow chamber into the internal space of the housing.
Figure 5:
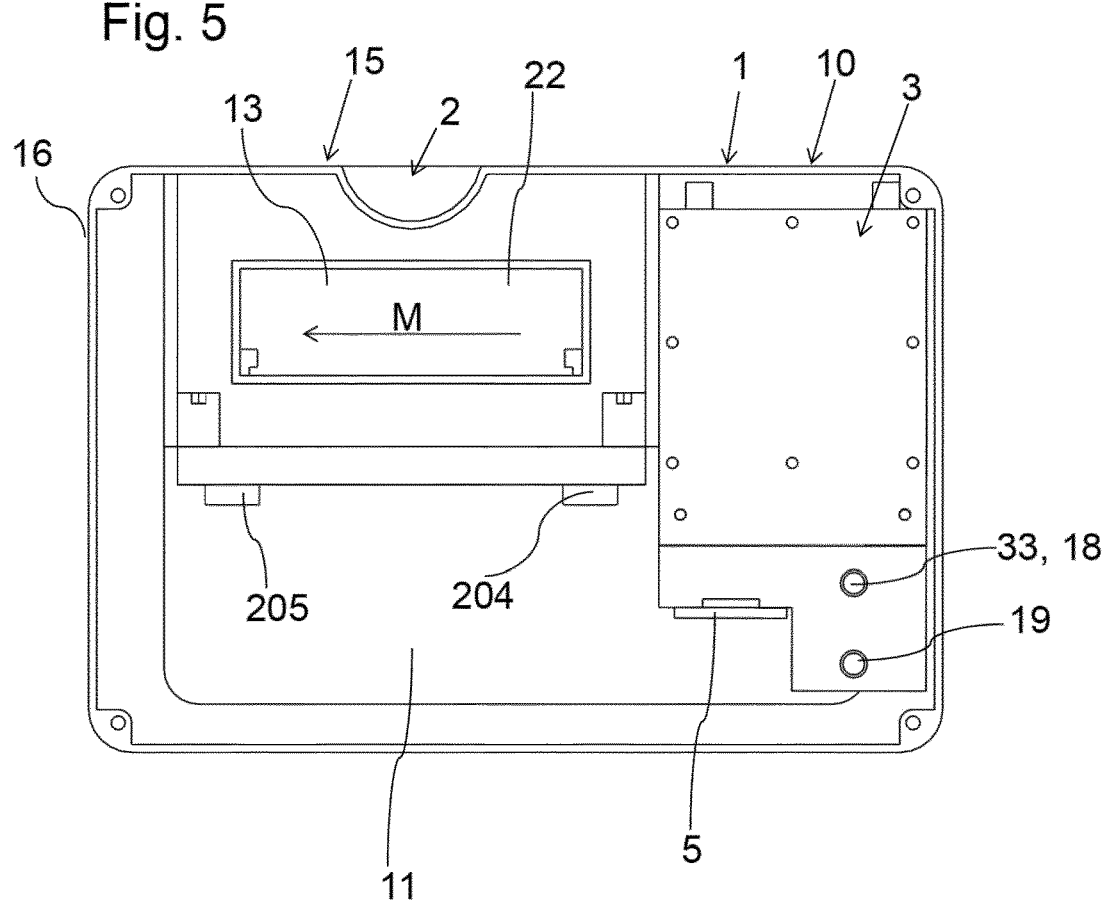
FIG. 5 shows a plan view onto the top wall of the housing of the cell culture device according to the invention with the top wall removed in order to show the components arranged inside said internal space such as the heater and the flow chamber.
Figure 15:
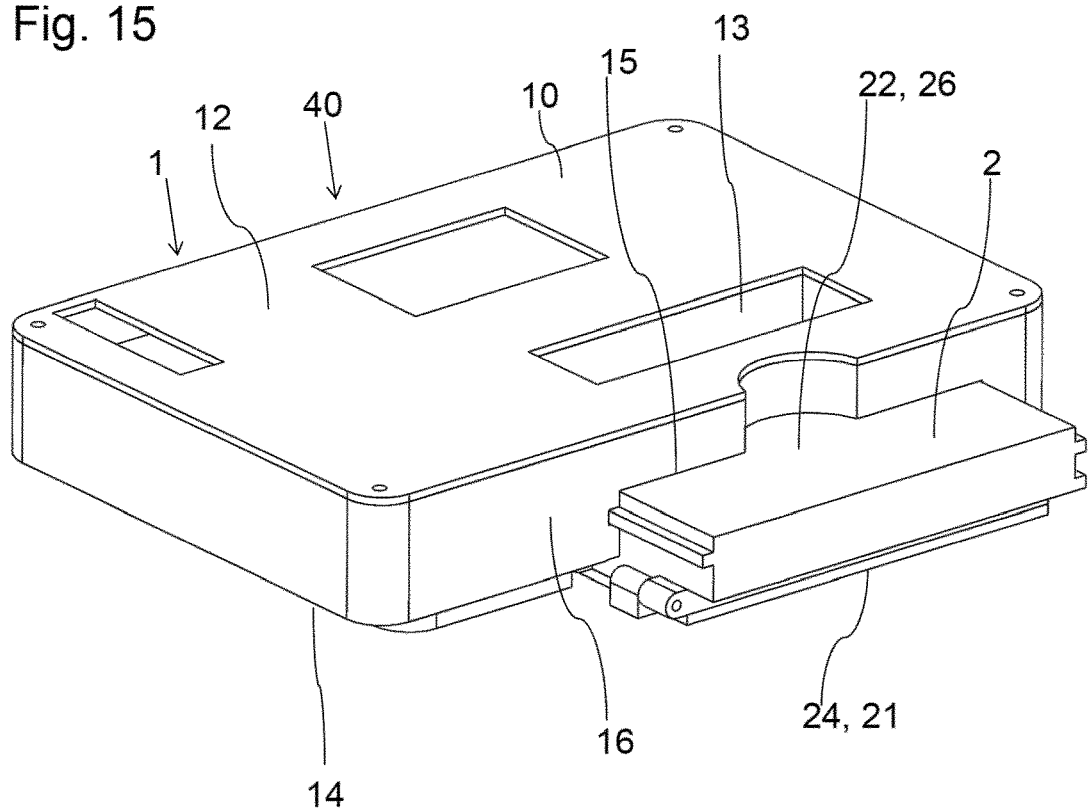
FIG. 15 shows the flow chamber being inserted into the housing or removed from the housing of the cell culture device.

For sliding the flow chamber into and out of the internal space 11 of the housing 10, which sliding is shown in FIG. 15, the housing 10 particularly comprises a recess 15 that is e.g. formed into a lateral wall 16 of the housing that connects the opposing top and bottom wall 12, 14 of the housing 10 as well as into the bottom wall 14 as indicated e.g. in FIGS. 4 and 15.

For easy sliding of the flow chamber 2, the latter comprises at least two guide rails 23 as shown e.g. in FIG. 6. The guide rails 23 can be discontinued by other components such as a latch 27 that will be described in more detail below. Each guide rail 23 is configured to engage into a groove 17 formed in the housing 10 (cf. FIG. 4), so that a guided sliding movement is facilitated by the engaging guide rails 23 and grooves 17.

Figure 7:
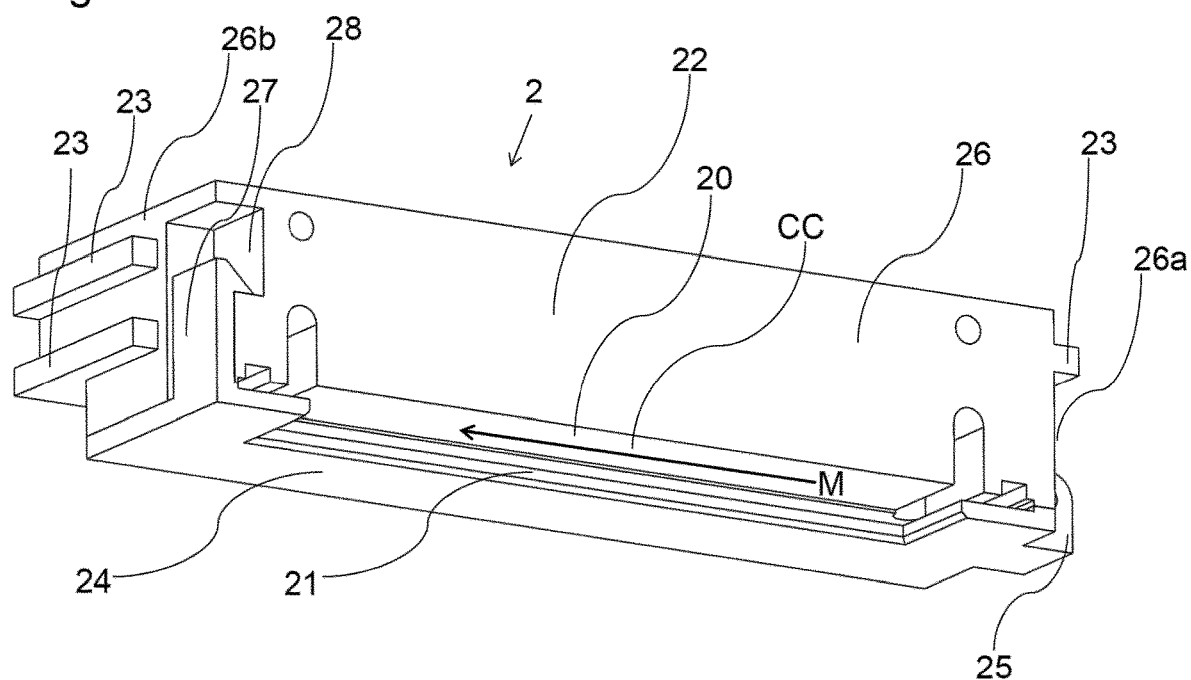
FIG. 7 shows a perspective cross sectional view of the flow chamber.

Particularly, according to FIG. 6, the flow chamber May 2 comprise a single guide rail 23 on a first lateral side 26*a* of a body 26 of the flow chamber 2 as well as two parallel (discontinued) guide rails 23 on a second lateral side 26*b* of said body 26, which second lateral side 26*b* faces away from the first lateral side 26*a*. As shown in FIG. 7, said body 26 comprises a recess 20 forming an internal space 20 of the flow chamber 2 on a side of the body 26 that faces a door 24 that can be hinged (via hinges 25) to said first lateral side 26*a* of the body 26. The door 24 can be closed (e.g. so as to seal the internal space 20) using said latch 27 which is configured to engage with a recess 28 formed into the second lateral side 26*b* in order to close the door 24 and seal the internal space 20 of the flow chamber 2.

Particularly, for observing the cell culture CC residing in the internal space 20 of the flow chamber 2, the door 24 comprises said first transparent wall region 21 (e.g. in the form of a window of the door 24), while the opposing body 26 of the flow chamber 2 comprises or forms said second transparent wall region 22. Particularly, the entire body 26 can be transparent.

Further, particularly, when the door 24 is closed and the flow chamber 2 is slid into the recess 15, the door 24 is flush with the bottom side 14 of the housing 10 or slightly recessed with respect to the bottom side 14.

Further, as already stated above, the flow chamber 2 comprises an inlet port 200 for injecting said fluid medium M into the flow chamber 2 and an outlet port 201 for discharging said fluid medium M out of the flow chamber 2, wherein particularly said ports 200, 201 are arranged on a back side 26*c* of said body 26, which back side 26*c* connects said first lateral side 26*a* with said second lateral side 26*b* of the body 26 of the flow chamber 2 (cf. FIGS. 6 and 8).

Further, as indicated in FIGS. 6 and 8, the flow chamber 2 comprises on the back side 26*c* of the body 26 a first one-way valve 202 and a second one-way valve 203 (e.g. for pushing air bubbles out of the flow chamber 2). Particularly, the first valve 202 may serve for filling a fluid medium into the flow chamber 2 and the second valve 203 may serve for flushing a liquid medium out of the flow chamber 2 and subsequently pushing air bubbles out of the flow chamber 2.

In order to establish flow connections between the internal space 20 of the flow chamber 2 and the first and second flow paths P1, P2 inside the internal space 11 of the housing 10 of the cell culture device 1, the flow chamber 2 is further configured to be slid into said recess 15 of the housing 10 with the inlet port 200 and the outlet port 201 ahead so that the inlet port 200 engages with a connector 204 of the first flow path P1 and the outlet port 201 engages with a connector 205 of the second flow path P2 (cf. e.g. FIGS. 1 and 6) and a flow connection between the inlet port 200 and the first flow path P1 and between the outlet port 201 and the second flow path P2 is established when the flow chamber 2 is completely slid into the recess 15.

Furthermore, as indicated in FIG. 2A, the first flow path P1 is connected to an inlet 18 arranged on the housing 10, particularly on the top wall 12 of the housing 10, whereas the second flow path P2 is connected to an outlet 19 arranged on the housing 10, particularly on the top wall 12 of the housing 10. Here, the inlet 18 is configured to be connected to a first conduit for guiding said fluid medium M into the first flow path P1, while the outlet 19 is configured to be connected to a second conduit for discharging said fluid medium M coming from the flow chamber 2 out of the second flow path P2.

The first conduit may connect to a container for storing said fluid medium M while the second conduit may connect to a waste bin for discarding the fluid medium. Alternatively, both conduits may connect to said container for recycling the fluid medium, i.e. the fluid medium M is pumped into the internal space 20 of the flow chamber 2 via the first flow path P1 and out of the internal space 20 of the flow chamber 2 back into the container via the second flow path P2. Particularly, the pump 4 can be arranged in the first and or second flow path P1. P2 inside or outside the internal space 11 of the housing 10.

Figure 17:
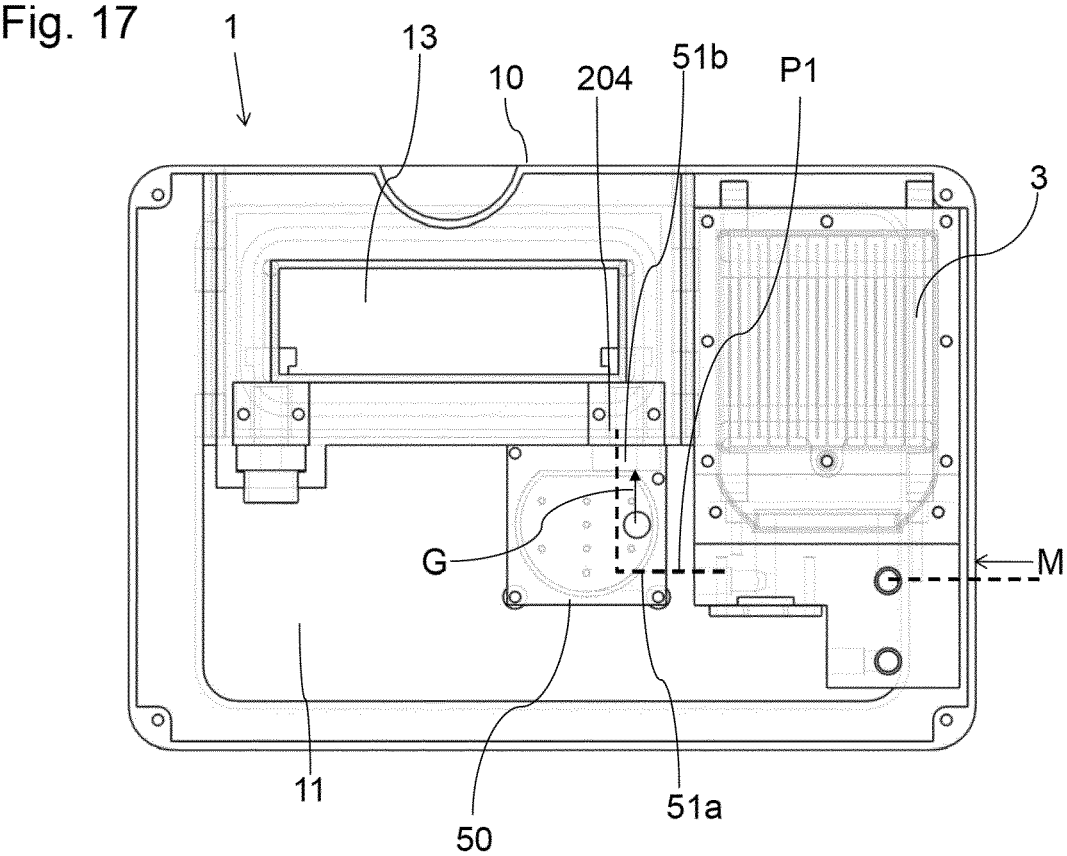
FIG. 17 shows an embodiment of the cell culture device comprising a bubble trap.
Figure 18:
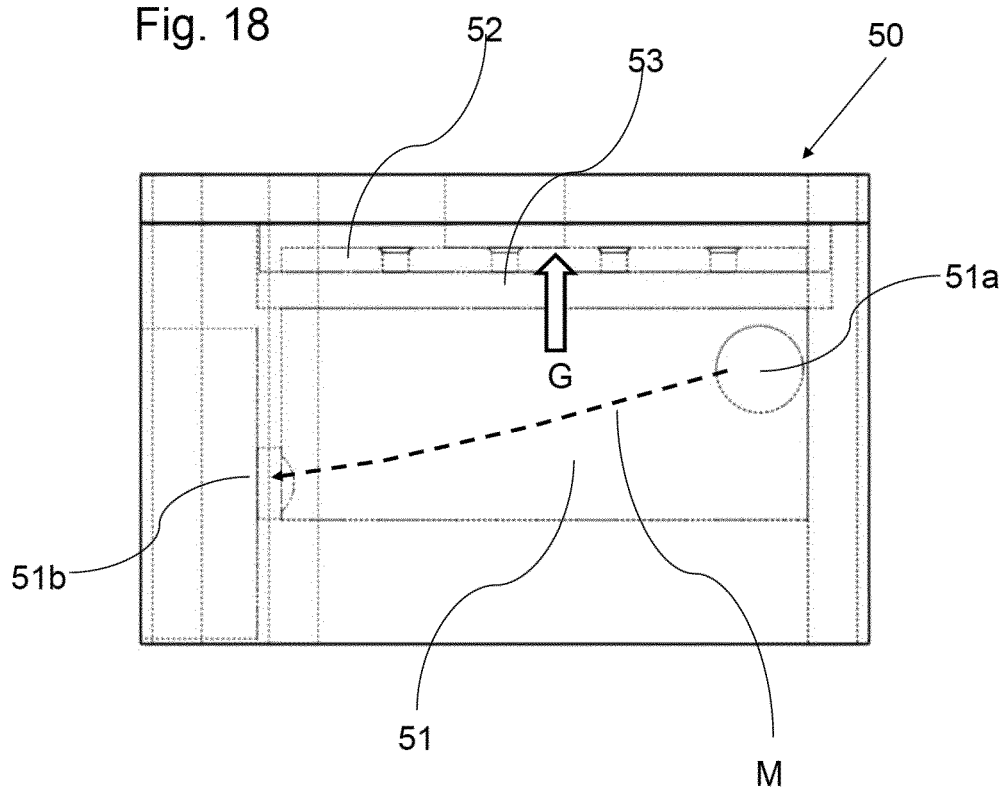
FIG. 18 shows a side view of the bubble trap of FIG. 17.
Figure 19:
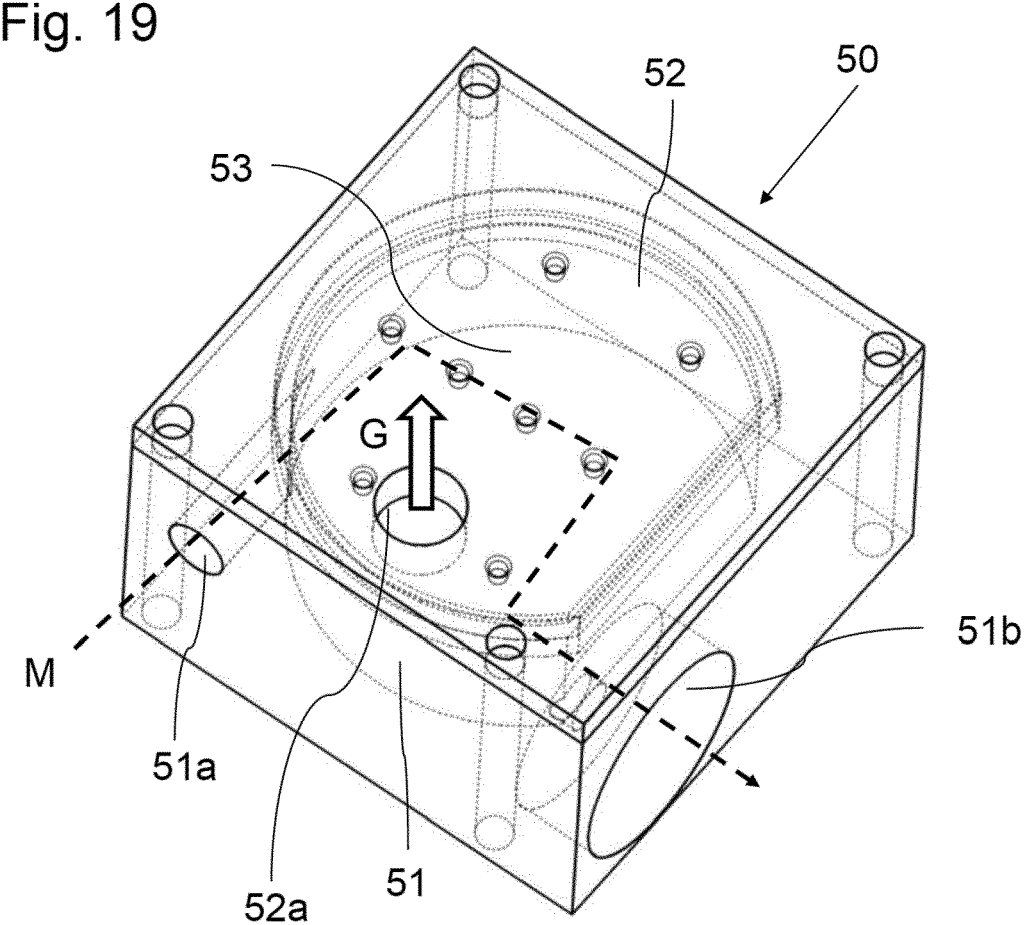
FIG. 19 shows a perspective view of the bubble trap shown in FIGS. 17 and 18.

Furthermore, as shown in FIGS. 17 to 19, the cell culture device 1 can comprise a gas bubble trap 50 arranged in the internal space 11 of the housing 10 and configured for removing bubbles of a gaseous phase G from the fluid medium M.

The bubble trap 50 may comprise a separate bubble trap housing that is arranged in said internal space 11 and particularly comprises a first volume 51 and an adjacent second volume 52 on top of the first volume 51, wherein the first and the second volume 51, 52 are separated by a semi-permeable membrane 53 which is impermeable to the fluid medium M but permeable for said gaseous phase G so that bubbles of the gaseous phase G can rise from the first volume 51 via the membrane 53 into the second volume 52 and are thus removed from the fluid medium M.

As can be seen from FIG. 17, the first volume 51 of the bubble trap 50 forms a section of the first flow path P1.

Particularly, the first volume 51 comprises an inlet 51*a* connected to the outlet 34 of the heater 3 as well as an outlet 51*b* connected to the connector 204 so that fluid medium M can be passed from the heater 3 to the first volume 51 of the bubble trap 50 and from the first volume 51 to the flow chamber 2, wherein bubbles of said gaseous phase G rise from the first volume 51 into the second volume 52 via the membrane so as to remove them from the first flow path while the liquid phase of the medium M is retained by the membrane 53.

Further, the second volume 52 is particularly smaller than the first volume 51 and particularly comprises a smaller pressure than the first volume 51 during operation of the cell culture device 1. Particularly, the second volume 52 is under a vacuum, therefore increasing the amount of gas (e.g. air) that can pass through the semi-permeable membrane 53. Further, for removing the gaseous phase G from the second volume 52 of the bubble trap 50, the second volume comprises an outlet 52*a* for removing said gaseous phase G from the bubble trap 50. Particularly, a pump can be connected to said outlet 52*a* so that the bubbles/gaseous phase G can be removed via the pump.

Figure 20:
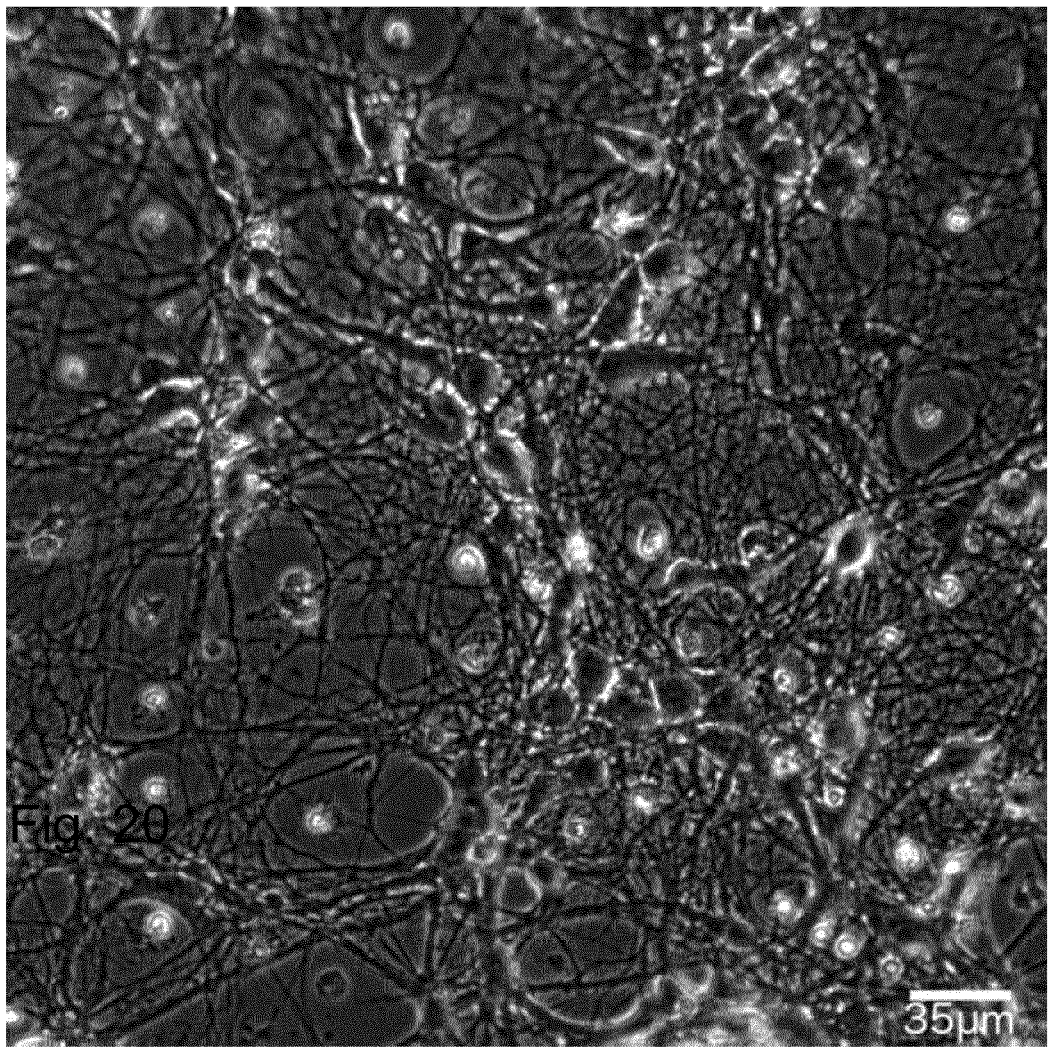
FIG. 20 shows primary neurons at 20× magnification, recorded on a cell culture device according to the present invention.
Figure 20:
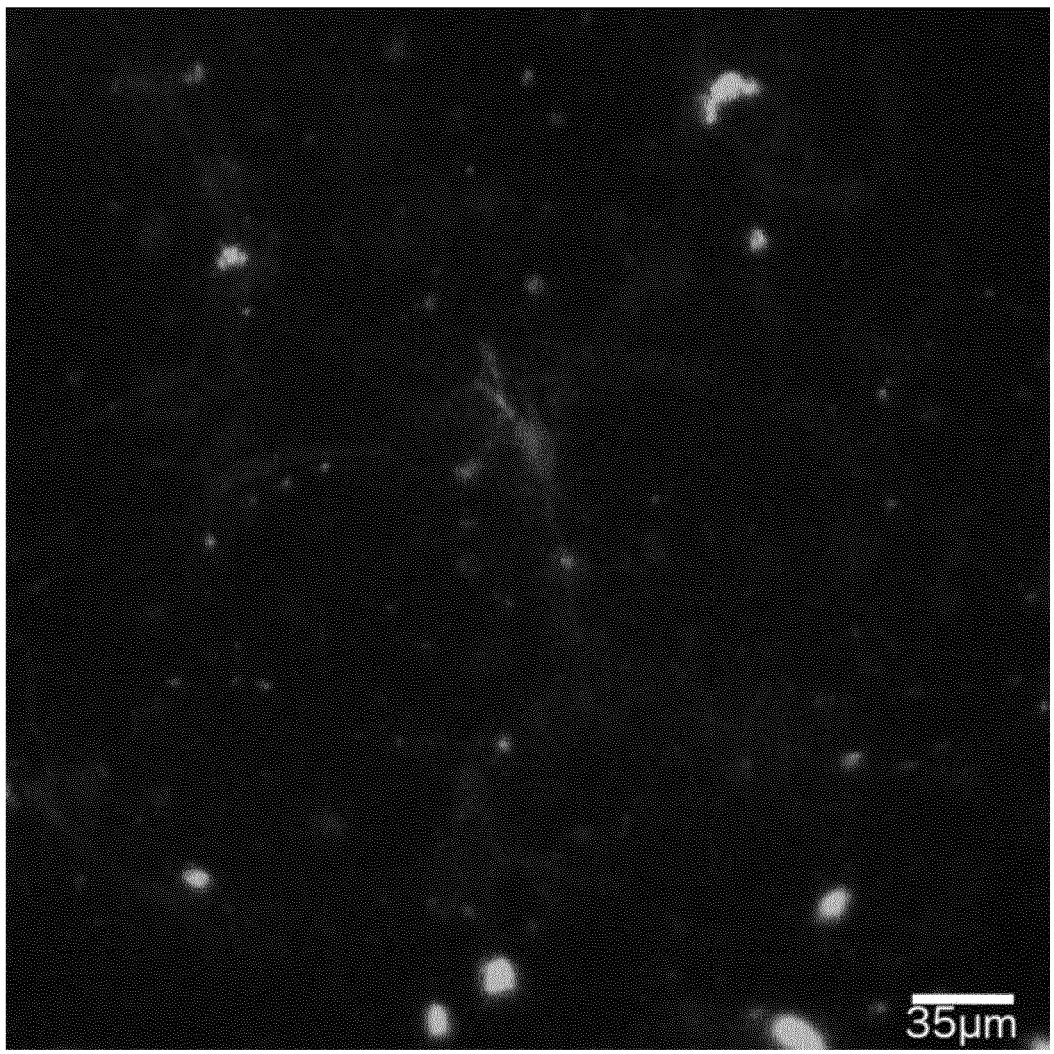
Figure 20:
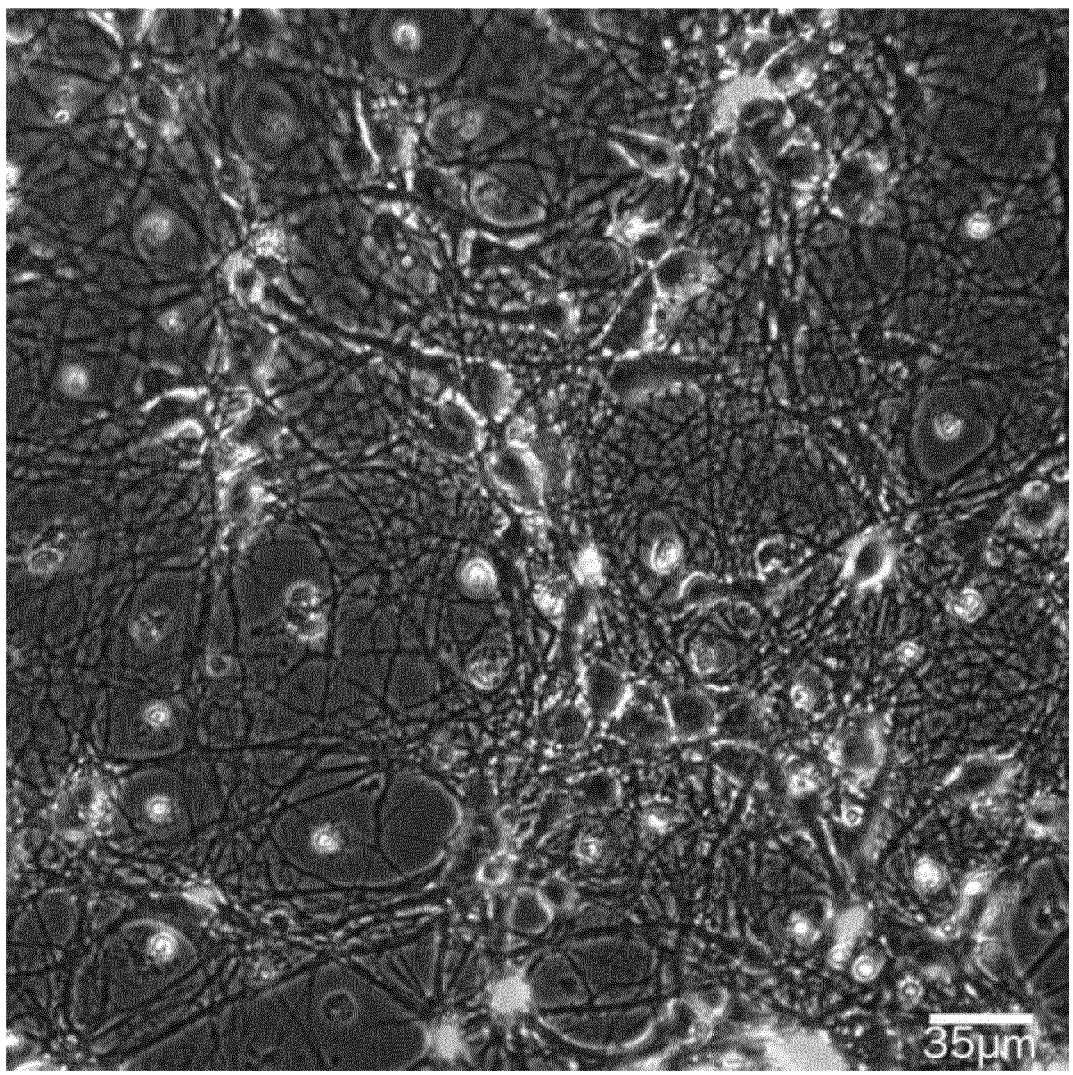

Finally, as an example, FIG. 20 shows primary Neurons at 20× magnification, recorded using a cell culture device according to the present invention while being exposed to a shear stress of 2.5 dyn/cm$^2$. Shown is the phase contrast image (A), the GFP Signal (B) and the overlay of both (C) after 800 s of shear exposure. The dissociated hippocampal neuron culture was obtained from C57B6/JjRj (Janvier Labs, France) mice. Time-mated mice were euthanized at day 16.5 of gestation (E 16.5) and embryos, their brains and then hippocampi were dissected under sterile conditions and digested using Tryple Select reagent (Gibco) 25 min. at 37 C. Obtained hippocampal neurons were plated at density 50,000/cm$^2$ in Neurobasal medium (Gibco) supplemented with 2% of Gibco B-27 on poly-D-lysine (100 ug/ml; Sigma) coated glass slides.

The invention claimed is:

1. A cell culture device (1) for use with an optical microscope, comprising
a housing (10) that is configured to be placed onto a stage of an optical microscope in front of an objective of the microscope, the housing enclosing an internal space (11) of the housing (10), wherein the housing (10) further comprises a top wall (12) comprising a window (13) and an opposing bottom wall (14), and wherein the housing comprises a recess (15),
a removable flow chamber (2) enclosing an internal space (20) configured to accommodate a cell culture (CC) comprising living biological cells, wherein the flow chamber (2) is configured to be inserted into the internal space (11) of the housing (10) by sliding the flow chamber (2) into the recess (15) and to be removed from the housing (10) for arranging the cell culture in the flow chamber (2) by sliding the flow chamber out of the recess (15), wherein the flow chamber (2) is further configured to guide a flow of a fluid medium (M) through the internal space (20) of the flow chamber (2) so that the fluid medium (M) can contact the cell culture (CC) and flow along the cell culture (CC), and wherein the flow chamber (2) further comprises a first and a second transparent wall region (21, 22) for observing the cell culture (CC) arranged in the internal space (20) of the flow chamber (2), wherein the transparent wall regions face (21, 22) said window (13) when the flow chamber (2) resides in said recess (15) of said housing (10) and allow light to pass through the housing via the transparent wall regions (21, 22) and the window (13),
a heater (3) arranged in the internal space (11) of the housing (10) for heating said fluid medium (M) to be guided through the flow chamber (2),
a first flow path (P1) arranged in the internal space (11) of the housing (10) configured to guiding said fluid medium (M) through said heater (3) and towards the flow chamber (2) when the flow chamber (2) resides in the recess (15), and a second flow path (P2) arranged in the internal space (11) of the housing (2) for guiding said fluid medium (M) away from the flow chamber (2) when the flow chamber (2) resides in the recess (15), wherein sliding the flow chamber (2) out of the recess causes the flow chamber (2) to be disconnected from said flow paths (P1, P2) and thereby from the heater (3),
a pump (4) for pumping said fluid medium (M) through the first flow path (P1) into the internal space (20) of the flow chamber (2) and through the second flow path (P2) out of the internal space (20) of the flow chamber (2) when the flow chamber (2) is inserted into the internal space (11) of the housing (10), and
wherein the flow chamber (2) comprises a door (24) being hinged to a body (26) of the flow chamber (2), which body (26) comprises a recess (20) formed therein forming the internal space (20) of the flow chamber (2), wherein said door (24) comprises said first transparent wall region (21), and wherein said body (26) of the flow chamber (2) comprises or forms said second transparent wall region (22), and wherein the door (24) is flush with the bottom wall (14) of the housing (10) when the flow chamber (2) is inserted into the internal space (11) of the housing (10).

2. The cell culture device according to claim 1, characterized in that the cell culture device (1) further comprises a temperature sensor (5) arranged in the internal space (11) of the housing (10) so that the temperature sensor (5) is in thermal contact with the fluid medium (M) guided through the first flow path (P1) for measuring the temperature of the fluid medium (M).

3. The cell culture device according to claim 1, characterized in that the cell culture device (1) further comprises a control unit (6) that is configured to control the heater (3) such that an actual value of the temperature of the fluid medium (M) measured with the temperature sensor (5) approaches a desired value of the temperature of the fluid medium (M).

4. The cell culture device according to claim 3, characterized in that the cell culture device (1) further comprises a flow sensor (7) for determining a flow rate of the fluid medium (M).

5. The cell culture device according to claim 4, characterized in that the control unit (6) is configured to control said pump (4) such that an actual value of the flow rate of the fluid medium measured with the flow sensor (7) approaches a desired value of the flow rate of the fluid medium (M).

6. The cell culture device according to claim 1, characterized in that the pump (4) is arranged in the internal space (11) of the housing (10) or that the pump (4) is an external pump being arranged outside said internal space (11) of the housing (10).

7. The cell culture device according to claim 1, characterized in that the housing (10) comprises a lateral wall (16) connecting the top wall (12) to the bottom wall (14) of the housing (10), wherein said recess (15) is formed into the bottom wall (14) and the lateral wall (16) of the housing (10).

8. The cell culture device according to claim 1, characterized in that the flow chamber (2) comprises at least two guide rails (23) which are each configured to engage with an associated groove (17) formed into the housing (10) for guiding the flow chamber (2) upon sliding the flow chamber (2) into and out of said recess (15).

9. The cell culture device according to claim 1, characterized in that the flow chamber (2) comprises an inlet port (200) for injecting said fluid medium (M) into the flow chamber (2) and an outlet port (201) for discharging said fluid medium (M) out of the flow chamber (2).

10. The cell culture device according to claim 9, characterized in that the flow chamber (2) is configured to be slid into said recess (15) with the inlet port (200) and the outlet port (201) ahead so that the inlet port (200) engages with a connector (204) of the first flow path (P1) and the outlet port (201) engages with a connector (205) of the second flow path (P2) and a flow connection between the inlet port (200) and the first flow path (P1) and between the outlet port (201) and the second flow path (P2) is established when the flow chamber (2) is inserted into the internal space (11) of the housing (10).

11. The cell culture device according to claim 1, characterized in that the height (H) of the housing is smaller than 25 mm or equal to 25 mm, and/or that the breadth (B) is smaller than 160 mm or equal to 160 mm, and/or that the depth (D) is smaller than 110 mm or equal to 110 mm.

12. The cell culture device according to claim 1, characterized in that the cell culture device (1) comprises a gas bubble trap (50) configured for removing bubbles of a gaseous phase from the fluid medium (M).

13. The cell culture device according to claim 12, characterized in that the bubble trap (50) comprises a first and a second volume (51, 52), wherein the first and the second volume (51, 52) are separated by a semi-permeable membrane (53) which is impermeable to the fluid medium (M) but permeable for said gaseous phase.

14. The cell culture device of claim 13, characterized in that the first volume (51) forms a section of the first flow path (P1), wherein the first volume (51) comprises an inlet (51a) connected to an outlet (34) of the heater (3), and/or that the first volume (51) comprises an outlet (51b) connected to a connector (204) of the first flow path (P1).

15. The cell culture device according to claim 13, characterized in that the second volume (52) is smaller than the first volume (51).

16. The cell culture device according to claim 13, characterized in that the second volume (52) comprises a smaller pressure than the first volume (51).

17. The cell culture device according to claim 13, characterized in that the second volume (52) of the bubble trap (50) comprises an outlet (52a) for removing said gaseous phase from the bubble trap (50).

18. A method for observing a cell culture (CC) using a cell culture device (1) according to claim 1 and a microscope (40), wherein a cell culture (CC) is arranged in the flow chamber (2) and the flow chamber (2) is inserted into the internal space (11) of the housing (10) of the cell culture device (1), and wherein the housing (10) of the cell culture device (1) is arranged on a stage (43) of the microscope (40) in front of an objective (41) of the microscope (40).

19. A cell culture device (1) for use with an optical microscope, comprising
 a housing (10) that is configured to be placed onto a stage of an optical microscope in front of an objective of the microscope, the housing enclosing an internal space (11) of the housing (10), wherein the housing (10) further comprises a top wall (12) comprising a window (13) and an opposing bottom wall (14), and wherein the housing comprises a recess (15),
 a removable flow chamber (2) enclosing an internal space (20) configured to accommodate a cell culture (CC) comprising living biological cells, wherein the flow chamber (2) is configured to be inserted into the internal space (11) of the housing (10) by sliding the flow chamber (2) into the recess (15) and to be removed from the housing (10) for arranging the cell culture in the flow chamber (2) by sliding the flow chamber out of the recess (15), wherein the flow chamber (2) is further configured to guide a flow of a fluid medium (M) through the internal space (20) of the flow chamber (2) so that the fluid medium (M) can contact the cell culture (CC) and flow along the cell culture (CC), and wherein the flow chamber (2) further comprises a first and a second transparent wall region (21, 22) for observing the cell culture (CC) arranged in the internal space (20) of the flow chamber (2), wherein the transparent wall regions face (21, 22) said window (13) when the flow chamber (2) resides in said recess (15) of said housing (10) and allow light to pass through the housing via the transparent wall regions (21, 22) and the window (13),
 a heater (3) arranged in the internal space (11) of the housing (10) for heating said fluid medium (M) to be guided through the flow chamber (2),
 a first flow path (P1) arranged in the internal space (11) of the housing (10) configured to guiding said fluid medium (M) through said heater (3) and towards the flow chamber (2) when the flow chamber (2) resides in the recess (15), and a second flow path (P2) arranged in the internal space (11) of the housing (2) for guiding said fluid medium (M) away from the flow chamber (2) when the flow chamber (2) resides in the recess (15), wherein sliding the flow chamber (2) out of the recess causes the flow chamber (2) to be disconnected from said flow paths (P1, P2) and thereby from the heater (3),
 a pump (4) for pumping said fluid medium (M) through the first flow path (P1) into the internal space (20) of the flow chamber (2) and through the second flow path (P2) out of the internal space (20) of the flow chamber (2) when the flow chamber (2) is inserted into the internal space (11) of the housing (10), and wherein the flow chamber (2) comprises a door (24) configured to cover a body (26) of the flow chamber (2), which body (26) comprises a recess (20) formed therein forming the internal space (20) of the flow chamber (2), wherein said door (24) comprises said first transparent wall region (21), and wherein said body (26) of the flow chamber (2) comprises or forms said second transparent wall region (22), and wherein the door (24) is flush with the bottom wall (14) of the housing (10) when the flow chamber (2) is inserted into the internal space (11) of the housing (10).

* * * * *